(12) United States Patent
Hutchison, III et al.

(10) Patent No.: US 8,497,069 B2
(45) Date of Patent: Jul. 30, 2013

(54) AMPLIFICATION AND CLONING OF SINGLE DNA MOLECULES USING ROLLING CIRCLE AMPLIFICATION

(75) Inventors: Clyde A. Hutchison, III, Rockville, MD (US); Hamilton O. Smith, Reisterstown, MD (US)

(73) Assignee: Synthetic Genomics, Inc., San Diego, CA (US)

( * ) Notice: Subject to any disclaimer, the term of this patent is extended or adjusted under 35 U.S.C. 154(b) by 464 days.

(21) Appl. No.: 11/919,515

(22) PCT Filed: May 1, 2006

(86) PCT No.: PCT/US2006/016349
§ 371 (c)(1),
(2), (4) Date: Oct. 29, 2007

(87) PCT Pub. No.: WO2006/119066
PCT Pub. Date: Nov. 9, 2006

(65) Prior Publication Data
US 2009/0176280 A1    Jul. 9, 2009

Related U.S. Application Data

(60) Provisional application No. 60/675,850, filed on Apr. 29, 2005, provisional application No. 60/722,070, filed on Sep. 30, 2005, provisional application No. 60/725,300, filed on Oct. 12, 2005.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC .............................. 435/6, 91.2, 6.12
See application file for complete search history.

(56) References Cited

U.S. PATENT DOCUMENTS

| | | | |
|---|---|---|---|
| 5,616,478 A | | 4/1997 | Chetverin et al. |
| 5,744,299 A | * | 4/1998 | Henrickson et al. ............... 435/6 |
| 6,617,137 B2 | * | 9/2003 | Dean et al. .................... 435/91.2 |
| 2001/0029036 A1 | * | 10/2001 | Landers et al. ............. 435/91.1 |
| 2005/0130173 A1 | * | 6/2005 | Leamon et al. ................... 435/6 |

FOREIGN PATENT DOCUMENTS

| | | |
|---|---|---|
| EP | 1 482 036 | 12/2004 |
| WO | WO-94/09127 A | 4/1994 |
| WO | WO-00/15779 | 3/2000 |
| WO | WO-2004/096288 A | 11/2004 |
| WO | WO-2005/028629 | 3/2005 |

OTHER PUBLICATIONS

Hutchison III, C.A. et al., "Cell-free cloning using phi29 DNA polymerase," Proceedings of the National Academy of Sciences of the United States of America, vol. 102, No. 48, pp. 17332-17336, Nov. 29, 2005.
Fire, A. et al., "Rolling replication of short DNA circles," Proceedings of the National Academy of Sciences of USA, National Academy of Science, Washington, DC, vol. 92, No. 10, pp. 4641-4645, 1995.
Liu, D. et al., "Rolling Circle DNA Synthesis: Small Circular Oligonucleotides as Efficient Templates for DNA Polymerases," Journal of the American Chemical Society, American Chemical Society, Washington, DC, vol. 118, No. 7, pp. 1587-1594, 1996.
Rubin, E. et al., "Convergent DNA synthesis: a non-enzymatic dimerization approach to circular oligodeoxynucleotides," Nucleic Acids Research, Oxford University Press, Surrey, GB, vol. 23, No. 17, pp. 3547-3553, Sep. 11, 1995.
European Search Report dated Mar. 28, 2008 issued in EP 06 75 1837.
Andersson et al., Analytical Biochemistry (1996) 236:107-113.
Dean et al., Genome Research (2001) 11(6):1095-1099.
Detter et al., Genomics (2002) 80(6):691-698.
Mitra et al., Nucleic Acids Research (1999) 27(24):e34.
Nakano et al., Journal of Biotechnology (2003) 102(2):117-124.
Nelson et al., Biotechniques (2002) pp. S44-S47.
Rector et al., Journal of Virology (2004) 78:4993-4998.

* cited by examiner

*Primary Examiner* — Kenneth R. Horlick
*Assistant Examiner* — Joyce Tung
(74) *Attorney, Agent, or Firm* — DLA Piper LLP (US)

(57) ABSTRACT

The present invention relates, e.g., to a method for amplifying a small number of copies (e.g. a single copy) of a single-stranded circular DNA molecule (e.g. having a size of about 5-6 kb) by an isothermal rolling circle mechanism, using random or partially random primers and a F29-type DNA polymerase. The method, which can also be used for amplifying DNAs by non-rolling types of multiple displacement amplification, comprises incubating the reaction components in a small volume, e.g. about 10 µl or less, such as about 0.6 µl or less. The degree of amplification can be about 109 fold, or higher. A method for cell-free cloning of DNA, using the rolling circle amplification method of the invention, is described.

25 Claims, 9 Drawing Sheets

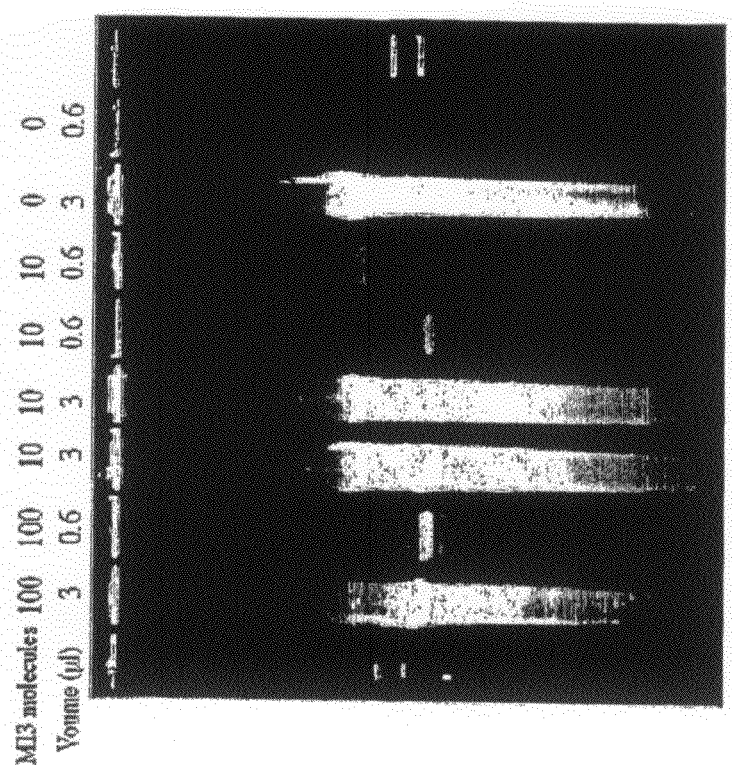
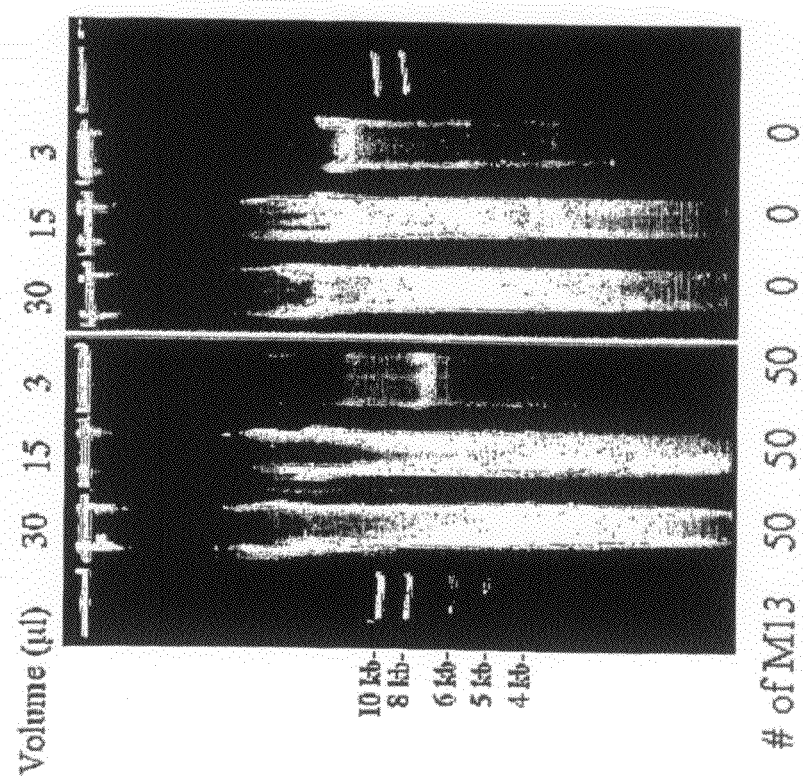
FIG. 3A
FIG. 3B

```
          SmaI    BamHI      BstXI(12)          M13 or1(40)                                              M13f (18)
TGCAT CCCGGG GGATCC GTTAC CCAGCACACTGG GTTCTTAATAGTGGACTCTTGTTCCAAACTGGAACAACA ACTGCCGTCGTTTACA
ACGTA GGGCCC CCTAGG CAATG GGTCGTGTGACC CAAGAATTATCACCTGAGAACAAGTTTGACCTTGTTGT TGACCGGCAGCAAATGT

Lac repressor (25)           Spacer(8)    I-SceI(18)               BbvCI(7)    NotI(8)
GGAATTGTGA GCGGATAACA ATTCC ATGAGAGT   TAGGG ATAA|CAGGGTAAT CC|TCA GC GC|GGCC GC
CCTTAACACT CGCCTATTGT TAAGG TACTCTCA   ATCCC|TATT GTCCCATTA GG AGT|CG CG CCGG|CG M13r(18)           PI-PspI(30)                       BstXI(12)      BamHI   SmaI
CAGGAAACAGCTATGACC TGGCAAACAGCTA TTAT|GGGTATTATGGT CCAGTGTGCTGG TAAGT GGATCC CCCGGG TTGCA
GTCCTTTGTCGATACTGG ACCGTTTGTCGAT|AATA CCCATAATACCCA GGTCACACGACC ATTCA CCTAGG GGGCCC AACGT
```

FIG. 9

SEQUENCE LISTING

```
<160> NUMBER OF SEQ ID NOS: 25

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1 hhhhhc                                                                       6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2 dddddg                                                                       6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 vvvvva                                                                       6

<210> SEQ ID NO 4
<211> LENGTH: 6
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4 bbbbbt                                                                      6

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5 hhhhhh                                                                      6

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 rrrrrr                                                                      6

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 yyyyyy                                                                      6

<210> SEQ ID NO 8
<211> LENGTH: 6
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(5)
<223> OTHER INFORMATION: a, c, g, t, unknown or other

<400> SEQUENCE: 8 nnnnnh                                                                      6

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(6)
<223> OTHER INFORMATION: a, c, g, t, unknown or other

<400> SEQUENCE: 9
```

-continued

```
nnnnnn                                                                6

<210> SEQ ID NO 10
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 mmmmmm                                                                6

<210> SEQ ID NO 11
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11 kkkkkk                                                                6

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12 ssssss                                                                6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 wwwwww                                                                6

<210> SEQ ID NO 14
<211> LENGTH: 240
<212> TYPE: DNA
<213> ORGANISM: Artificial Sequence
<220> FEATURE:
<223> OTHER INFORMATION: Description of Artificial Sequence: Exemplary
      cloning vector

<400> SEQUENCE: 14
tgcatcccgg gggatccgtt acccagcaca ctgggttctt taatagtgga ctcttgttcc      60
aaactggaac aacaactggc cgtcgtttta caggaattgt gagcggataa caattccatg     120
agagttaggg ataacagggt aatcctcagc gcggccgcca ggaaacagct atgacctggc     180
aaacagctat tatgggtatt atgggtccag tgtgctggta agtggatccc ccgggttgca     240

<210> SEQ ID NO 15
<211> LENGTH: 240
<212> TYPE: DNA
<213> ORGANISM: Artificial Sequence
<220> FEATURE:
```

```
<223> OTHER INFORMATION: Description of Artificial Sequence: Exemplary
      cloning vector

<400> SEQUENCE: 15
tgcaacccgg gggatccact taccagcaca ctggacccat aatacccata atagctgttt      60
gccaggtcat agctgtttcc tggcggccgc gctgaggatt accctgttat ccctaactct     120
catggaattg ttatccgctc acaattcctg taaaacgacg gccagttgtt gttccagttt     180
ggaacaagag tccactatta aagaacccag tgtgctgggt aacggatccc ccgggatgca     240

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cactgccttt ccagcaca                                                    18

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgacggaaa ggtc                                                        14

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cattgccttt ccagcaca                                                    18

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtaacggaaa ggtc                                                        14

<210> SEQ ID NO 20
<211> LENGTH: 46
<212> TYPE: DNA
<213> ORGANISM: Unknown
<220> FEATURE:
<223> OTHER INFORMATION: Description of Unknown: Unknown
      polymerase clone

<400> SEQUENCE: 20
tcgaacggct gcggacgaca gggcgagcgc cagaacgttt tttacc                     46

<210> SEQ ID NO 21
```

```
<211> LENGTH: 48
<212> TYPE: DNA
<213> ORGANISM: Unknown
<220> FEATURE:
<223> OTHER INFORMATION: Description of Unknown: Unknown
      polymerase clone

<400> SEQUENCE: 21
tcgcaacggc tgcggacgac cagggcgagc gccagaacgt tttttacc            48

<210> SEQ ID NO 22
<211> LENGTH: 48
<212> TYPE: DNA
<213> ORGANISM: Unknown
<220> FEATURE:
<223> OTHER INFORMATION: Description of Unknown: Unknown
      polymerase clone

<400> SEQUENCE: 22
tcgcaacggc gccggacgac cagggcgagc gccagaacgt tttttacc            48

<210> SEQ ID NO 23
<211> LENGTH: 736
<212> TYPE: DNA
<213> ORGANISM: Unknown
<220> FEATURE:
<223> OTHER INFORMATION: Description of Unknown: Unknown
      polymerase clone
<220> FEATURE:
<221> NAME/KEY: modified_base
<222> LOCATION: (13)..(13)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (315)..(315)
<223> OTHER INFORMATION: a, c, g, t, unknown or other
<220> FEATURE:
<221> NAME/KEY: modified_base
<222> LOCATION: (678)..(679)
<223> OTHER INFORMATION: a, c, g, t, unknown or other
<220> FEATURE:
<221> NAME/KEY: modified_base
<222> LOCATION: (686)..(686)
<223> OTHER INFORMATION: a, c, g, t, unknown or other
<220> FEATURE:
<221> NAME/KEY: modified_base
<222> LOCATION: (699)..(699)
<223> OTHER INFORMATION: a, c, g, t, unknown or other
<220> FEATURE:
<221> NAME/KEY: modified_base
<222> LOCATION: (707)..(707)
<223> OTHER INFORMATION: a, c, g, t, unknown or other
<220> FEATURE:
<221> NAME/KEY: modified_base
<222> LOCATION: (710)..(710)
<223> OTHER INFORMATION: a, c, g, t, unknown or other
<220> FEATURE:
<221> NAME/KEY: modified_base
<222> LOCATION: (723)..(723)
<223> OTHER INFORMATION: a, c, g, t, unknown or other
<220> FEATURE:
<221> NAME/KEY: modified_base
<222> LOCATION: (730)..(730)
<223> OTHER INFORMATION: a, c, g, t, unknown or other

<400> SEQUENCE: 23
gttctgttac tgngnatgct gccttagcag gtttattaa tagtgctttt ggtcaaactc    60
acactaatct gtttatggat aaatattttg ctaatccacc acaaaataag ttgtgcaaat  120
ttattgaaaa gtactcataa ttagaaaaat ccaattacag tatgaatgct aaaaaaacta  180
```

```
attaataatt tcgatcatta aacaattaat tatttgttat aaaaaatttt gtaattaatt      240
caattaaaaa tggtaaatct ctcctcccaa atgaaagtga caaaaatatt gtaatttctt      300
aaaaataaat aaaantttgt taatagtgga actacattaa tctacttata tgaaattaaa      360
aaagaattaa ccgataaaaa tataggttaa tttgagaaga atatattgaa cagattaata      420
aacaaaaaca taattcaaat ttaagttttg ctattgtgaa tagcaaaaca actatttcat      480
cattaattct gaaaacaagt ttaacgctta aaataatatg ctaaacaaca gaaaataatt      540
aagactttgt tagatataaa gataagaact tatttatcta aaaaaacaat gagtttgcag      600
atgacatgca aaatgaaaat cgggccttat tggatgatta aatttaccaa ctagacgaat      660
aaaaaatagc ctgattannt tattcnttag ccttggatna atagacnttn aaaagttata      720
atnagccgcn ttttta                                                     736

<210> SEQ ID NO 24
<211> LENGTH: 75
<212> TYPE: DNA
<213> ORGANISM: Unknown
<220> FEATURE:
<223> OTHER INFORMATION: Description of Unknown: Unknown
      polymerase clone

<400> SEQUENCE: 24
tttttagttt tagccacttt ttcgtaaaaa aaaaaaaaaa aaagcagttt ttgctatttt       60
agactaaaag tggtt                                                       75

<210> SEQ ID NO 25
<211> LENGTH: 74
<212> TYPE: DNA
<213> ORGANISM: Unknown
<220> FEATURE:
<223> OTHER INFORMATION: Description of Unknown: Unknown
      polymerase clone

<400> SEQUENCE: 25
ttttagtcta aaatagcaaa aattgctttt tttttttttt ttttacgaaa aagtggctaa       60
aactaaaaat aatt                                                        74
```

AMPLIFICATION AND CLONING OF SINGLE DNA MOLECULES USING ROLLING CIRCLE AMPLIFICATION

This application claims priority to U.S. Provisional Application Ser. No. 60/675,850, filed Apr. 29, 2005, U.S. Provisional Application Ser. No. 60/722,070, filed Sep. 30, 2005, and U.S. Provisional Application Ser. No. 60/725,300, filed Oct. 12, 2005, which are incorporated by reference herein in their entirety.

This invention was made with U.S. government support (DOE grant number DE-FG02-02ER63453). The government has certain rights in the invention.

FIELD OF THE INVENTION

This invention relates, e.g., to methods for amplifying DNA molecules and for cell-free cloning.

BACKGROUND INFORMATION

A number of methods have been developed for exponential amplification of nucleic acids. These include the polymerase chain reaction (PCR), ligase chain reaction (LCR), self-sustained sequence replication (SSR), nucleic acid sequence based amplification (NASBA), strand displacement amplification (SDA), and amplification with Qβ replicase (see, e.g., Birkenmeyer et al. (1991) *J. Virological Methods* 35, 117-126 and Landegren (1993) *Trends Genetics* 9, 199-202).

Current methods of PCR amplification involve the use of two primers which hybridize to the regions flanking a nucleic acid sequence of interest such that DNA replication initiated at the primers will replicate the nucleic acid sequence of interest. By separating the replicated strands from the template strand with a denaturation step, another round of replication using the same primers can lead to geometric amplification of the nucleic acid sequence of interest. Among other disadvantages, PCR amplification is prone to sequence errors; is limited to amplification of short DNA segments; and cannot proceed continuously, but must be carried out by subjecting the nucleic acid sample to multiple cycles, at shifting temperatures.

Isothermal DNA amplification methods have been described in which such thermal cycling is not required. These methods take advantage of the properties of DNA polymerases such as Φ29 (Phi 29) DNA polymerase, which are highly processive and are able to displace strands of DNA that lie in their path.

One such isothermal method, sometimes termed multiple displacement amplification (MDA), has been used to amplify large molecular weight linear DNA, such as genomic DNA. In one form of this method, two sets of primers are used that are complementary to opposite strands of nucleotide sequences flanking a target sequence. Amplification proceeds by replication initiated at each primer and continuing through the target nucleic acid sequence, with the growing strands encountering and displacing previously replicated strands. In another form of the method, a random set of primers is used to randomly prime a sample of genomic nucleic acid. The primers in the set are collectively, and randomly, complementary to nucleic acid sequences distributed throughout nucleic acid in the sample. Amplification proceeds by replication initiating at each primer and continuing so that the growing strands encounter and displace adjacent replicated strands. In another form of the method concatenated DNA is amplified by strand displacement synthesis with either a random set of primers or primers complementary to linker sequences between the concatenated DNA. Synthesis proceeds from the linkers, through a section of the concatenated DNA to the next linker, and continues beyond, with the growing strands encountering and displacing previously replicated strands.

Rolling circle amplification (RCA) is a multiple displacement amplification method which can be performed on DNA molecules which are circles or which can be circularized and are of a suitable size. In one embodiment, a double-stranded nucleic acid is circularized (e.g. by insertion of a nucleic acid molecule of interest into a linear vector to form a circular molecule) and one strand is nicked, such that one strand is continuous and the other strand is discontinuous. One or more primers are annealed to the continuous strand of the circular vector (a single-stranded circular DNA molecule), and are used to initiate DNA copying. As each primer annealed to the circular template DNA is extended, the growing strand encounters and displaces previously replicated DNA to produce a continuous sequence of tandem copies of the circle. Secondary priming events can subsequently occur, resulting in an exponential amplification. When different primers are used, one or more for each strand, a cascade of strand displacement occurs, resulting in the sort of pinwheel structure shown in FIG. 1. Eventually, the single strands of amplified DNA are converted to double-stranded DNA.

Molecular cloning of DNAs (e.g. having an unknown sequence) is routinely carried out using plasmid, phage, or viral vectors that replicate inside cells. Such methods are sometimes referred to as in vivo cloning methods. Methods of in vivo cloning are described, e.g., in Sambrook et al., Molecular Cloning. A Laboratory Manual, 2nd Edition. Cold Spring Harbor Laboratory Press, Cold Spring Harbor, N.Y., 1989. In vivo cloning methods are laborious, requiring steps of electroporating DNA into cells, plating the cells, picking colonies, growing the picked colonies overnight, and preparing template from those cultures. These processes are time consuming, costly and not amenable to high-density formats. Furthermore, certain DNA sequences have proven to be difficult to clone in vivo, because, for example, they are toxic to *E. coli* or other host cells in which they are to be cloned, or for other reasons that are not well-understood.

Methods of in vitro (cell-free) cloning have been described which obviate some of the problems of in vivo cloning. For example, a method has been described in which individual DNA molecules are cloned in solution by serial dilution and subsequent PCR amplification from tubes containing single molecules (Lukyanov et al. (1996) *Nucleic Acid Research* 24, 2194-2195. Another method has been described for cloning RNA populations derived from single RNA molecules in an immobilized medium (Chetverina et al. (1993) *Nucleic Acids Research* 21, 2349-2353). Another method—the "polony" method—has been described for in situ PCR amplification of individual molecules (Mitra et al. (1999) *Nucleic Acids Res* 27, e34. Among other drawbacks, such methods result in a high mutation rate and stuttering at sequences of low complexity, especially homopolymer tracts.

The inventors describe herein a high fidelity, cell-free method to clone single copies of DNAs (e.g. of unknown sequence), using isothermal rolling circle amplification primed by multiple primers comprising random, partially random or defined sequences.

DESCRIPTION OF THE DRAWINGS

FIGS. 3A and 3B show that background synthesis is suppressed by reducing φ29 polymerase reaction volume. In FIG. 3A, φ29 polymerase reactions of 30 µl, 15 µl and 3 µl were assembled, each containing either 50 M13 single-stranded DNA molecules, or no template DNA. The reactions products were digested with Pst I and analyzed by gel electrophoresis. In FIG. 3B, the φ29 polymerase reactions were 3 µl or 0.6 µl, and each contained either 100 or 10 M13 single-stranded DNA molecules, or no template DNA, as indicated.

FIG. 5A (SEQ ID NOS 20-22, respectively, in order of appearance) shows sequencing of cell-free clones of synthetic φX174 molecules. Sequencing was performed following PCR amplification of single-molecule φ29 polymerase reactions. The same region is compared for a synthetic φX clone with a single base deletion (molecule 1), one with the wild-type sequence in this region (molecule 3), and natural φX DNA. FIG. 5B (SEQ ID NO: 23) shows direct sequencing of φ29 polymerase reaction products without PCR amplification. This figure shows the result of sequencing 18% of the product from a 600 nl reaction. FIG. 5C (SEQ ID NOS 24-25, respectively, in order of appearance) shows the sequence reads through an $A_{18}$ tract and the complementary $T_{18}$ tract on a molecule amplified by φ29 polymerase. Sequencing was performed directly on the cell-free φ29 polymerase cloned products, without PCR amplification.

FIG. 9 shows an exemplary cloning vector (SEQ ID NOS 14-15, respectively, in order of appearance) which is useful for cloning DNA molecules by a method of the invention.

DESCRIPTION OF THE INVENTION

Figure 1:
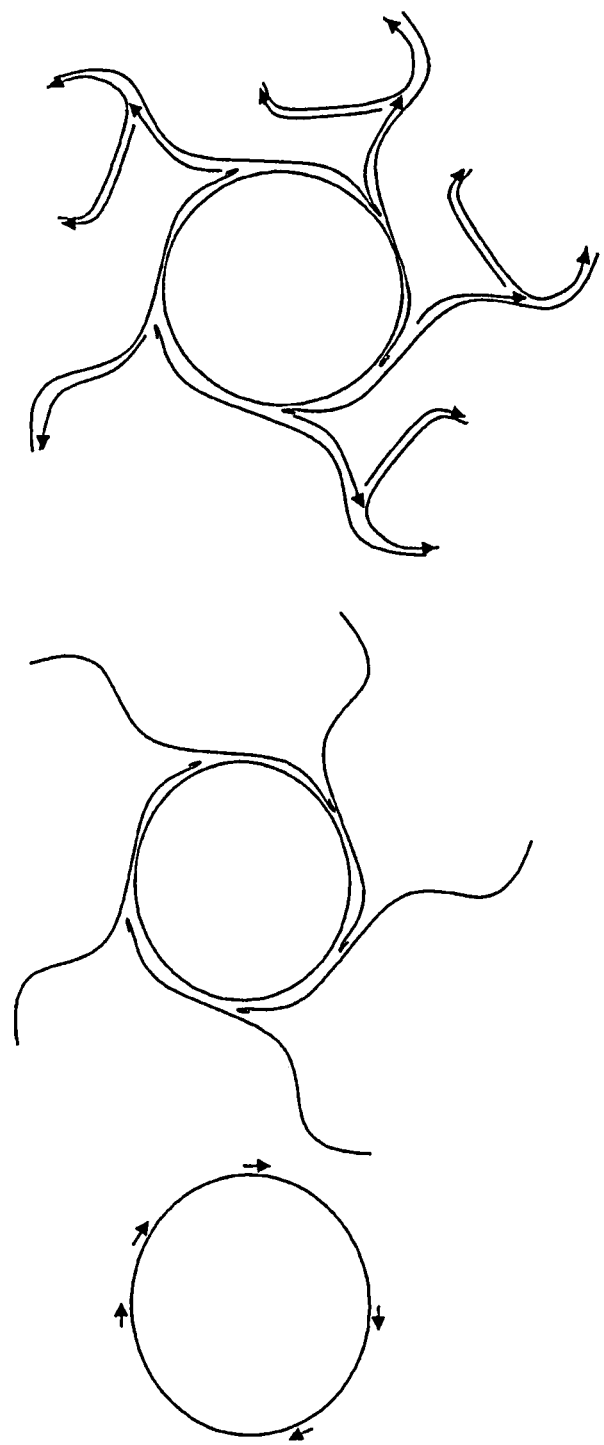
FIG. 1 is a cartoon (comparative) illustrating multiply-primed rolling circle amplification. Oligonucleotide primers complementary to the amplification target circle are hybridized to the circle. The 3' ends of the DNA strands are indicated by arrowheads to show the polarity of polymerization. The addition of DNA polymerase and deoxynucleoside triphosphates (dNTPs) to the primed circle results in the extension of each primer, and displacement of each newly synthesized strand results from elongation of the primer behind it. Secondary priming events can subsequently occur on the displaced product strands of the initial rolling circle amplification step. This drawing is not to scale, as circular templates are typically about 5-6 kb, and product strands average about 70 kb in length.

The present invention relates, e.g., to a method for high fidelity, isothermal amplification of small amounts, including a single copy, of a DNA template of interest and/or for cell-free cloning of the DNA of interest. A method of the invention can be used to amplify any DNA, using a strand displacing, processive DNA polymerase which elongates in a 5' direction from a suitable primer. The method can be applied to a variety of types of amplification, including MDA, specifically the sub-type of MDA, RCA. In one embodiment, the template is single-stranded circular DNA having, for example, a size of about 5-8 kilobases (kb), e.g. about 5-6 kb; and the template is amplified by a Φ29-type DNA polymerase by a rolling circle mechanism, using random or partially random primers (e.g. hexamer primers) or defined primers (e.g. decamer primers).

Initial attempts by the inventors to amplify a low amount of template by rolling circle amplification resulted in the production of undesirable background synthesis. See, e.g., Example II and FIG. 2. This background did not appear if primers were omitted from the reaction mixture. Without wishing to be bound by any particular mechanism, it is suggested that the background results from copying simple sequence units built up from the primer population. The inventors have developed methods to reduce or eliminate this background synthesis (to improve the signal to noise ratio).

One way to reduce this background is to reduce the volume in which a fixed amount of a small number of template molecules is amplified, while keeping the concentration of other components of the reaction mixture (e.g. primers, polymerase, nucleotides, etc.) constant. Example II shows that a substantial reduction in background was observed after reducing the reaction volume from 30 to 3 µl, and an even greater reduction was observed by reducing the volume to 0.6 µl or less.

A second way to reduce this background is to use primers which contain base compositions that prevent nonspecific amplification. Without wishing to be bound by any particular mechanism, it is suggested that certain primers (e.g. hexamers) cannot base pair their 3' nucleotides and thus cannot anneal and build up simple sequence units that can be copied. For example, the primer set H*C (a mixture of the 243 sequences HHHHHC (SEQ ID NO:1), wherein H=A, C, or T) contains no G's, so the 3° C. would not be expected to base pair with other copies of the primer. If background arises by action of Φ29 polymerase on the primers, this primer would be expected to generate reduced background. Example VIII shows, e.g., that this primer does, indeed, result in reduced background.

A third way to reduce this background is to combine reducing the volume of the reaction mix with the use of primers of the invention.

The reduction of background synthesis allows a DNA template of interest to be amplified to a high degree. Without wishing to be bound by any particular mechanism, it is suggested that the high levels of amplification occur because there is little if any interference by a background of smaller DNAs (e.g., there is little if any competition for enzymes or substrates, and the small background DNAs do not take over the reaction). Using the amplification methods of the invention, the inventors have achieved amplification of single molecules (e.g. about 5-8 kb circular DNAs), during a single amplification reaction (in a single reaction chamber), by a factor of approximately $10^9$. When the amplification method is RCA, $10^9$ copies of the entire template can be made. When longer and/or linear DNAs are amplified, by non-rolling circle types of MDA, only portions of the template are generally amplified. However, the net mass of amplified DNA can be about $10^9$ fold that of the starting material. In embodiments of the invention, the template DNA is amplified by a factor of at least about $10^8$, e.g. at least about $2 \times 10^8$, $5 \times 10^8$, $10^9$, $2 \times 10^9$, $5 \times 10^9$, $10^{10}$, $2 \times 10^{10}$, or more. The method of the invention can generate microgram amounts of DNA from single DNA molecules. If the amplified DNA in a reaction mixture is then further diluted into a fresh reaction mixture and allowed to undergo further cycles of amplification, the yield is increased. This method for extending the yield of amplified DNA is discussed further below.

The disclosed cell-free method for amplifying and/or cloning templates of interest (e.g. DNAs whose sequence is unknown) provides many advantages. A single round of multiply primed rolling circle replication results in a large amplification of the circular vector, orders of magnitude greater than a single cycle of PCR replication and other amplification techniques in which each cycle is limited to a doubling of the number of copies of a target sequence. The method is rapid and provides high yields of high fidelity amplified DNA and allows for rapid cloning. For example, the time required to construct a library of cloned sequences by a cell-free cloning method of the invention is about 3 days less than the time required to construct an equivalent library by conventional cloning in *E. coli*. Because the method eliminates the need for cloning in *E. coli* or other hosts, it permits cloning of DNAs that are resistant to in vivo cloning. Such resistant DNAs include, e.g., synthetic phage genomes carrying lethal mutations, such as frameshifts in essential genes; sequences which are toxic to the host; sequences prone to replication errors; certain environmental samples; etc. Amplification methods of the invention do not produce mutant "jackpots" or stuttering at homopolymer tracts. Furthermore, the in vitro cloning procedure obviates the need to separate the amplified DNA from other cellular components, including cellular DNA, which requires time-consuming and ineffective procedures. The reaction need not result in the complex mixture of nucleic acids that often occurs during cell-based molecular cloning. Also, because the inventive method is performed entirely in vitro, it can be automated and scaled-up in ways that are not possible in cell-based molecular cloning. For example, the amplification process is amenable to automation where multiple reactions are carried out simultaneously in a small area, without the need of human intervention.

A method of the invention can be applied to a various uses, including, for example, DNA sequencing (e.g. genome sequencing) and/or the preparation of genes or genomes of interest. For example, single copies of DNA fragments from a gene or genome of interest, including synthetically produced DNA fragments, can be amplified by a method of the invention and sequenced; errors in the amplified copies can be corrected, if necessary; and the amplified DNA fragments can be assembled to generate part or all of the gene or genome or interest. The ability to rapidly generate accurate fragments, which can serve as cassettes, in a high throughput manner allows one to, "mix and match" a large number of variants of each cassette and thus to assemble readily a variety of combinations of mutated or variant genes or genomes.

The inventive method for reducing background during the amplification of single copies of DNA can also be used to reduce background synthesis in a variety of other methods of DNA amplification, including amplification of DNA from single cells (e.g. bacterial or other cells which contain about 2-3 identical chromosomes, or partial chromosomes which are in the process of replicating) or of DNA from organisms, such as certain viruses, which contain a plurality of different chromosomes (templates).

One aspect of the invention is a method for amplifying no more than one copy of a DNA template (for amplifying part or all of a DNA template, wherein no more than one copy of the DNA template is present at the start of the incubation). The method comprises contacting the DNA with a strand-displacing, processive DNA polymerase and a set of random or partially random primers, in a very low volume, e.g. of about 10 µl or less, under conditions that are effective for promoting DNA strand displacement, at a substantially isothermal temperature, wherein the amplification is performed a) with a low primer concentration, e.g. of about 50 µM or less; and/or b) under conditions such that the amplified DNA is sufficiently free from background that it can be used directly, without further purification, for sequencing, restriction enzyme analysis, hybridization analysis, in vitro recombination with other DNA molecules to assemble portions of a gene or genome, etc. These or other tests can be used to confirm that the amplified DNA is relatively free of background contamination.

A desirable concentration of primer in the reaction is about 50 µM or less ("about" 50 µM includes 40 µM to 60 µM). With too little primer, too little amplification will occur. With too much primer, background synthesis resulting from excess primer may occur. A skilled worker can vary the amount of primer to determine whether smaller or larger amounts of primer can be used, determining an optimal amount of amplification relative to background synthesis (signal to noise ratio).

Methods of the invention result in amplification of the DNA template. In one embodiment, the DNA template is amplified by multiple displacement amplification (MDA). When the template is longer than the length which can be elongated by a DNA polymerase having a particular processivity, the DNA amplified by MDA tends to be in the form of fragments which are shorter than the full-length template. In another embodiment, when the DNA template is circular and is small enough to be copied by a rolling circle mechanism, the DNA is amplified by rolling circle amplification (RCA) and the amplification product comprises two or more tandem copies of the template (see FIG. 1). (Of course, there may also be partial copies and single copies of the template, but these account for only a small fraction of the total amplified DNA product.)

The amplification product of RCA can be cleaved to linear molecules which are approximately the size of the DNA template (e.g. with a suitable restriction enzyme that cuts one time in the DNA template of interest or in a vector used to circularize the DNA). In a method of the invention, the background of undesirable small DNAs is so low that, if such an amplification product is digested to unit length copies of the DNA template, subjected to electrophoresis on a gel (e.g. an agarose gel, an acrylamide gel or any other suitable gel for fractionating DNAs of the size of the template), stained with a fluorescent dye (e.g. an intercalating dye, such as ethidium bromide, Syber GOLD or Syber GREEN (InVitrogen)), and illuminated with UV light, a discrete band of approximately the expected size for the unit length DNA can be visualized above background. This or other tests can be used to confirm that the amplified DNA is relatively free of background, and otherwise to determine the signal-to-noise ratio of amplification.

In one embodiment of the method, the amplification is performed in a single reaction chamber, and the DNA template is amplified by a factor of at least about $10^9$. For example, the DNA template is amplified until the amplified DNA reaches a degree of amplification of at least about $10^9$-fold. The DNA template may be amplified by a factor of at least about $5 \times 10^9$, at least about $10^{10}$, or more.

In embodiments of the invention, the DNA polymerase is a Φ29-type polymerase (e.g. a Φ29 polymerase), and/or the temperature of the reaction is about 30° C. The volume of the reaction mixture may be about 10 µl or less (e.g. about 5 µl, 2 µl, 1 µl, 0.6 µl, 0.2 µl, 0.064 µl, 0.01 µl, or 0.001 µl or less). The volume may be as small as the volume of an E. coli (about $3 \times 10^{-6}$ nl), or even less.

Random or partially random primers used in a method of the invention may have a length of between about 6 and about 20 nucleotides (nts), e.g. 6, 8, 10, 12, 14 or 16 nts, preferably hexamers. The primers may be resistant to exonuclease. For example, at least two nucleotides (e.g. at least three nucleotides) in each of the primers may be linked by a phosphorothioate linkage. For example, primers in a mixture of primers may be represented by the formula NNNN*N*N (SEQ ID NO:9), wherein N=A, G, C or T, and * indicates a phosphorothioate linkage.

In one embodiment, the DNA is formed from cDNA made from mRNA.

One embodiment of the invention is a method for amplifying a single copy of a circular, single-stranded DNA template of about 5-7 kb, comprising contacting the DNA with Φ29 DNA polymerase and a mixture of random or partially random primers at a concentration of about 50 µM or less, in a volume of about 0.6 µl or less, under conditions that are effective for promoting DNA strand displacement, at about 30° C.

In one embodiment of this method, when the reaction is carried out in a single reaction chamber; no more than one copy (molecule) of the DNA template is initially present in the starting reaction mixture; and the DNA template is amplified until it is reaches a degree of amplification of at least about $10^9$.

Another aspect of the invention is a method for amplifying a single copy of a DNA template, comprising circularizing the DNA template into a vector which contains between 2 and about 20 tandem copies of a first defined primer recognition sequence (e.g. a decamer) and, interspersed between those copies, between 2 and about 20 tandem copies of a second, complementary primer recognition sequence (e.g. a decamer); contacting the DNA with a strand-displacing, processive DNA polymerase and a set of primers which are complementary to the two primer sequences, under conditions that are effective for promoting DNA strand displacement, at a substantially isothermal temperature, wherein the amplification is performed a) with a primer concentration of about 5 µM; and/or b) in a volume of about 10 µl or less (e.g., about 0.6 µl or less, or about 0.06 µl or less).

In one embodiment of this method, the amplification is carried out in a single reaction chamber; no more than one copy (molecule) of the DNA template is initially present in the starting reaction mixture; and the DNA template is amplified until it is reaches a degree of amplification of at least about $10^9$. The defined primers may range in size from about 8 to about 20 nt (e.g. 8, 10, 12 or 14 nt); decamers are preferred. The concentration of defined primers can range from about 2 µM to about 10 µM. For decamers, a concentration of about 5 µM is suitable. The repeated sequences serve as multiple priming sites for the DNA polymerase.

Another aspect of the invention involves the amplification of DNA from a single cell, (e.g. a bacterial or other cell which contains about 1-3 identical chromosomes, or partial chromosomes which are in the process of replicating). These DNA molecules are too long to be amplified by RCA, and thus are amplified by other types of MDA. One embodiment of this method is a method for amplifying part or all of each of the DNA templates, comprising contacting the DNA molecules with a strand-displacing, processive DNA polymerase and a set of random or partially random primers, in a volume of 10 µl or less (e.g. about 0.6 µl or less, or about 0.06 µl or less), under conditions that are effective for promoting DNA strand displacement, at a substantially isothermal temperature, wherein the amplification is performed a) with a primer concentration of about 50 µM or less; and/or b) under conditions such that the amplified DNA is sufficiently free from background that it can be used directly, without further purification, for sequencing, restriction enzyme analysis, hybridization analysis, and/or in vitro recombination with other DNA molecules to assemble portions of a gene or genome, etc.

Amplification methods of the invention can be applied to any of a variety of uses.

In one embodiment, the method is a method of cell-free cloning (isolating and amplifying a single copy of a DNA of interest). A mixture of DNAs are circularized to form circular double-stranded (ds) DNAs, and subjected to a limit dilution (end point dilution) procedure, to obtain a solution which contains a single copy of a circular dsDNA of interest. This DNA molecule is then converted to a single-stranded (ss) circular DNA and is amplified by a rolling circle method of the invention. The DNA is thus cloned without ever having been subjected to an in vivo cloning procedure, involving growth/passage in a cell, such as a bacterium. The cloned DNA can then be subject to a variety of procedures, such as sequencing, restriction enzyme analysis, etc. without being subject to any further purification steps. This simplifies cloning and permits automation.

In one embodiment, the cloned, amplified DNA is sequenced. This method comprises converting a single copy of a DNA of interest to a single-stranded, circular DNA; amplifying the single-stranded circular DNA by a method of the invention; and sequencing the amplified DNA.

In another embodiment, the DNA template comprises adjacent portions of a gene or genome of interest. One can further amplify one or more additional DNA templates that comprise other adjacent portions of the gene or genome of interest, by a method of the invention, and assemble the amplified DNAs to form part or all of the gene or genome of interest.

Amplified DNA generated by a method of the invention can be further amplified as follows: An aliquot of the reaction mixture is diluted into a fresh reaction mixture which comprises DNA polymerase and a second mixture of primers (which can be random, partially random, or defined primers); and then the fresh reaction mixture is incubated under conditions that are effective for promoting DNA strand displacement, at a substantially isothermal temperature. In one embodiment, the first and second set of primers comprise sequences represented by different formulas. The reaction conditions in the fresh reaction mixture may otherwise be the same or different.

Methods of the invention can be adapted to high throughput procedures. For example, an, amplification method of the invention may be performed in an automated nanomolar system (such as a Parallab 350 machine). In one embodiment, the components of the reaction mixture are combined in a nanochamber (i.e., a small reaction container which holds a very small volume, such as a volume equal to or less than about 500 nl, 200 nl, 64 nl, or less); incubated at a substantially isothermal temperature; and the amplified DNA is removed from the nano-chamber, wherein all of the steps are performed robotically.

One aspect of the invention is a system for performing an amplification method of the invention, which comprises (a) reagents for carrying out the amplification, and (b) an automated nanomolar device, which comprises means (e.g. robotic means) for combining the reaction components (e.g. in a nano-chamber); for incubating the reaction components at a fixed temperature (isothermally), using a suitable heating unit; and for removing the amplified DNA. The device need not contain the elements required for thermocycling; in fact, a devise that can only heat solutions to one or a few predetermined temperatures could be less expensive to build and maintain than a device with the complex machinery required for carrying out repeated thermocycles.

Another aspect of the invention is a linear double-stranded vector for use in cell-free cloning of a DNA of interest, which consists of no more than about 200 bp (e.g. no more than about 100 bp, no more than about 60 bp, or even smaller), and whose ends can ligate to compatible sequences on either end of a linear DNA template to be circularized and amplified. For example, the compatible sequences can be restriction enzyme sites, such as Type IIS restriction sites, which allow the DNA inserts to be excised from the vector without including sequences on the ends that were not present in the starting DNA template. One such restriction enzyme is BstXI. Because such vectors do not need to replicate in a cell, they can lack a number of elements found in vectors used for in vivo cloning. For example, a vector of the invention can lack an origin of replication, a selectable marker, etc. For sequencing libraries, the vector can be as small as about 60 nt (e.g., just long enough to contain forward and reverse sequencing primers and a cloning site, such as BstXI, at either end).

In one embodiment of the invention, a vector as above contains between 2 and about 30 tandem copies (e.g. about 2, 4, 6, 8, 10, 12, 14 or more) of a first defined primer recognition sequence (e.g. 8-12 nt, such as a decamer) and, interspersed between those copies, between 2 to about 30 tandem copies of a second, complementary primer recognition sequence (e.g. 8-12 nt, such as a decamer). A skilled worker can design and test candidate primer sequences in order to identify sequences which produce little or no background amplification. A vector which contains such tandem copies is particularly suitable for cloning DNA molecules that are to be sequenced. If a vector is used which contains a single copy of a primer (facing in one or both directions), the sequencing can be initiated from the primer site.

In another embodiment of the invention, a vector as above further comprises one or more (e.g. all) of the following elements: a site (such as an M13 origin of replication or an enzyme such as BbvCI) which allows one strand of the DNA to be nicked and removed, leaving a single-stranded circle for amplification by a pbi29-type polymerase; a primer site (such as an M13 primer site or a repeated primer sequence as noted above) which allows sequencing into either end of a DNA insert; one or more homing endonuclease sites (such as PI-PspI and I-SceI), which permit linearization of the cloned DNA from within the vector sequence; a sequence that allows recovery of the DNA from mixtures of DNA (such as a Lac repressor site which can serve as a means of specifically binding the vector, using Lac repressor protein). An exemplary vector of this type is shown in Example IX and FIG. 9.

One aspect of the invention is a method for sequencing a linear double-stranded DNA of interest, comprising: inserting it into a cloning vector as above, thereby circularizing the DNA of interest; converting the double-stranded DNA to a single-stranded circle; amplifying the single-stranded circle by a rolling circle amplification method of the invention; and sequencing the amplified DNA.

In one embodiment of the invention, the amplification is carried out in a single reaction chamber (vessel), and the DNA template is amplified by a factor of at least about $2 \times 10^8$ (e.g. at least about $5 \times 10^8$, $10^9$, $2 \times 10^9$, $5 \times 10^9$, $10^{10}$, $2 \times 10^{10}$, or more). In one embodiment, the template DNA is no more than about 500 kb (e.g., no more than about 200, 100, 70, 50, 25, 10, 7, 5 or 3 kb, and may be substantially shorter) in size. For embodiments of the invention in which it is desirable to obtain a full or nearly full-length copy of the template (e.g. for cloning or sequencing the molecules), the size of the template is limited primarily by the processivity of the DNA polymerase. $\Phi 29$ polymerase, for example, has been reported to copy about 500,000 nt, so a DNA template that is 500 kb can be used in reactions employing that DNA polymerase. Preferably, the DNA template is in the form of a single-stranded DNA circle, and the amplification occurs by a rolling circle mechanism. In one embodiment, the DNA template is a single-stranded DNA circle between about 3 kb and 10 kb in length (in ranges described herein, the endpoints of the range are included), more preferably about 5-6 kb (e.g. between about 4.5 and about 6.5 kb) in length.

Methods for conducting reactions in small volumes will be evident to the skilled worker. For example, to reduce losses due to evaporation, the reactions may be conducted under a layer of oil, or in a sealed reaction chamber (such as a nano-capillary tube). In one embodiment, the volume of the reaction mixture is as small as the volume of a bacterial cell, such as an *E. coli* cell. This volume is about $3 \times 10^{-6}$ nl. Such a reaction can be carried out, e.g., by encapsulating the reaction mixture in a liposome, or in an artificial membrane. Methods to achieve such small reaction mixtures include, e.g., emulsifying the reaction mixture by sonicating in the presence of appropriate lipids, or other methods that will be evident to one of skill in the art. Reaction volumes below the lower limit for conventional pipettes can be achieved, for example, by using nanoliter pipetting devices such as Parallal 350 (Brooks Automation, Chelmsford, Mass.).

The small volumes of reaction mixes as described above result in a reduction in background synthesis, not only during the amplification of single copies of about 5-8 kb DNA by a rolling circle mechanism, but may also reduce the background when amplifying larger quantities of template; when amplifying large genomic DNAs (e.g. by MDA); etc.

Instead of reducing the volume of a reaction mixture in order to reduce the background, one can reduce the concentration of primers or polymerase (e.g. by about 10 to about 1000 fold), while keeping the volume of the reaction at the larger volume (e.g. at about 30 or 100 µl). A minimal seed quantity of primers and/or polymerase appears to be necessary in order to initiate the copying. The mole ratio of primers to template may be about $10^{15}$:1 or less (e.g. about $2 \times 10^{14}$, $10^{14}$, $10^{13}$, $10^{12}$, $10^{11}$, $10^{10}$, $10^9$, $10^8$, $10^7$, or $10^6$ to 1); and/or the molar ratio of polymerase to template may be about $1.5 \times 10^{10}$:1 or less (e.g., about $3 \times 10^9$:1, $10^9$:1, $10^8$:1, $10^7$:1, $10^7$:1, $10^6$:1, or for smaller volumes, such as on the order of a bacterial cell volume, about $10^3$:1, $10^2$:1, or 50:1).

In one embodiment, the mole ratio of primers to template is about $10^{16}$ or less. For example, in a 600 nl reaction mixture containing a single molecule of template and primers at a concentration of about 50 µM, the mole ratio of hexamer primers to template is about $2 \times 10^{14}$:1. For a 3 µl reaction, the ratio is about five times this, or about $10^{15}$:1; for a reaction volume about the size of an *E. coli* (about $3 \times 10^{-6}$ nl), the ratio is about $10^6$:1. The weight ratio of primers to template can be about $10^{13}$:1 or less. For example, the weight ratio of primers to template for hexamer primers and a single-stranded template that is about 6 kb, is about 1000 times less that the mole ratios, e.g., about $2\times10^{11}$:1 for a 600 nl reaction; about $10^{12}$:1 for a 3 µl reaction; and about $10^3$:1 for a $3\times10^{-6}$ nl reaction.

In one embodiment, the ratio of polymerase to template is about $1.5\times10^{11}$:1 or less. For example, for a 600 nl reaction as above, the mole ratio is about $3\times10^9$:1; for a 3 µl reaction, about $1.5\times10^{10}$:1; and for an *E. coli* sized reaction, about 50:1.

In methods of the invention, the signal to noise ratio following amplification is high. For example, the amount of a desired amplified DNA reaction product compared to background synthesis may be at least about 25% of background (e.g. compared to the total amount of background, or to the background of DNAs of approximately the size of the desired DNA). It may be, e.g. at least about 50% as much, at least about the same amount, at least twice as much, three times as much, five times as much, 100 times as much, or 200 times as much, etc. In any event, the relative amount of a desired amplified DNA compared to background is sufficient for use in further processes without a further purification step to remove the desired amplification product from background synthesis. The relevant concentration that is required will depend on the subsequent process.

Another aspect of the invention is a method for amplifying a DNA template in a reaction mixture, comprising contacting the DNA with a DNA polymerase and a set of random or partially random primers, under conditions that are effective for promoting DNA strand displacement, at a substantially isothermal temperature, wherein the mixture of primers is represented by HHHHHC (SEQ. ID NO:1), or HHHHHH (SEQ ID NO:5), wherein H=A, C or T. Use of such primers results in a reduction in background synthesis, not only during the amplification of single copies of about, 5 kb DNA by a rolling circle mechanism, but may also reduce the background when amplifying larger quantities of template; when amplifying large genomic DNAs (e.g. by MDA); etc.

The disclosed methods can be used to clone or amplify any nucleic acid molecule of interest. The nucleic acid molecules can come from any source, including a cellular or tissue nucleic acid sample, a subclone of a previously cloned fragment, mRNA, chemically synthesized nucleic acid, genomic nucleic acid samples, nucleic acid molecules obtained from nucleic acid libraries, specific nucleic acid molecules, and mixtures of nucleic acid molecules.

The lower size limit of a DNA that can be amplified by an RCA method of the invention is a function of the ability of the DNA to circularize. Thus, for example, DNA templates as small as about 100 bp can be amplified by the method; single stranded DNAs can be even smaller. The upper size limit of molecules that can be amplified by RCA is a function of the degree of processivity of the DNA polymerase. The enzyme must be able to traverse the circular DNA template for several rounds in order to achieve a significant amount of amplification. For example, Φ29 polymerase, which is reported to be able to copy about 70 kb of DNA, can readily traverse a circular template of about 7 kb for about 10 cycles. Circles of about 15-20 kb can be readily amplified by Φ29 polymerase. Under conditions which allow greater processivity, or by using a more processive enzyme, longer templates can be amplified. The templates which can be amplified by non-rolling circle MDA can be longer; the size is limited only by the processivity of the DNA polymerase. Thus, for example, a linear molecule of about 70 bk can be amplified by Φ29 polymerase.

The disclosed methods can be used to produce libraries of cloned nucleic acid molecules starting with a complex mixture of nucleic acid molecules to be represented in the library. For example, cDNA can be produced from all of the mRNA in a cellular sample and used to make a cDNA library, or a library of genomic DNA can be produced from a genomic nucleic acid sample. In one embodiment, synthetically prepared portions of a gene or genome of interest are amplified and assembled to form a synthetic gene or genome. In one embodiment, portions (fragments) of a genomic DNA of interest are shot-gun cloned into a vector by conventional means; the mixture of clones is diluted such that each sample of diluted DNA contains, on average, one molecule of cloned DNA; and the DNA in the samples are then amplified by a method of the invention.

In methods of the invention, the nucleic acid molecule to be amplified is generally inserted into a double-stranded vector that can be readily circularized (e.g. by blunt end ligation or by ligation via linkers or adaptors which have been added to the ends of the DNA), or the single-stranded molecule is circularized directly. Preferably the insertion into a vector is accomplished by ligation, although any suitable coupling mechanism can also be used. Single-stranded nucleic acid molecules, such as RNA, can be used by converting the molecule to be double-stranded. In the case of RNA molecules, this can be accomplished, for example, by producing a cDNA molecule of the RNA. Numerous methods are known for preparing and inserting nucleic acid molecules into vectors and any of these can be used to prepare nucleic acid molecules for use in the disclosed method (see, for example, Sambrook et al., Molecular Cloning. A Laboratory Manual, 2nd Edition, Cold Spring Harbor Laboratory Press, Cold Spring Harbor, N.Y., 1989, for a discussion of this and other molecular biology methods used in the present methods). In one embodiment, the nucleic acid molecule is prepared by generating sticky ends to facilitate insertion in a linear vector. This can be accomplished, for example by cleaving a nucleic acid molecule of interest, or a nucleic acid sample, with a restriction enzyme, or by adding linkers to the ends of nucleic acid molecules of interest that have, or can be processed to have sticky ends. One or both of the ends of the nucleic acid molecule can also be left blunt ended. The two ends of nucleic acid molecules to be used in the disclosed method can also be made different to allow directional insertion. For example, the ends can have different sticky ends, or have one sticky end and one blunt end.

A DNA is preferably cloned into a special, multipurpose cloning vector of the invention, which is designed to facilitate circularization of the target DNA and subsequent use of the products for sequencing, error correction (e.g. by using oligonucleotide mutagenesis), further amplification, or other purposes. Such vectors can be quite small (e.g. a few hundred base pairs or less) because they do not need to support replication in bacteria. Additional elements may be included in this tiny vector as desired. Some such vectors are discussed elsewhere herein.

In one embodiment of the invention, the DNA to be amplified is cloned into a small synthetic vector such as that described in Example IX. Following ligation into this vector, a nick can be introduced at the f1 origin of replication site (ori site) by treatment with the f1 gene 2 protein; or a nick can be introduced at a "nicking site" in the vector by treatment with the NEB nicking enzymes N. BsmI or N. BbvCIb. Following the nicking, one can heat the nicked DNA in order to melt the strands apart. Isolation of the circular single strands is not required. However, if desired, the single-stranded circles can be isolated by conventional methods before amplification.

Some methods to nick circular double-stranded vectors containing inserts and to isolate the intact single-stranded circles are described in U.S. Pat. No. 6,287,824 to Lizardi.

By manipulations such as those discussed above, a DNA of interest can be "converted" to the form of a single-stranded, circular DNA, suitable for amplification by a method of the invention.

Conditions which are "effective for promoting DNA strand displacement," as used herein, include, in addition to the presence of a suitable DNA polymerase, DNA template and primers, reaction components such as salts, co-factors, nucleotide pools etc. Such components are conventional and well-known. Some typical conditions for Φ29 amplification are described in Example I. The reactants do not appear to be limiting in the Examples herein, which contain enough of the four dNTPs to produce approximately 1 μg of DNA per 1 μl of reaction volume. See also Dean et al. (2001) *Genome Res.* 11, 1095-1099. The amplification reactions of the invention are carried out under "substantially isothermal" conditions, e.g. conditions under which the temperature does not vary more by than about 2-3° C. above or below a given temperature. The temperature and length of incubation time for a rolling circle amplification procedure is a function of the polymerase used, the reaction conditions, and the like. Phi29 polymerase has been reported to be stable and to exhibit linear kinetics for over 24 hours at 30° C., allowing for extended incubation periods. Preferably, for Φ29 polymerase, the incubation temperature is about 30° C. The term "about," as used herein, refers to plus or minus about 20%. Thus, about 30° C. includes 24° C. to 36° C. Preferably, the temperature is 30° C. plus or minus about 2-3° C. Generally, reactions using Φ29 polymerase are carried out at about 30° C. for about 4-6 hours, although shorter or longer times can also be used. A skilled worker can readily optimize the factors for an amplification procedure with a given DNA polymerase.

Conditions such that the amplified DNA is sufficiently free from background that it can be used directly, without further purification, for sequencing, restriction enzyme analysis, hybridization analysis, and/or in vitro recombination with other DNA molecules to assemble portions of a gene or genome include the conditions which are effective for promoting DNA strand displacement, as well as the presence of a suitable small volume and a suitable concentration of primer molecules.

Following the generation of tandemly repeated copies of the template by RCA, unit copies may be generated by cleaving the RCA product with a restriction enzyme that cuts only once in the template, e.g. that cuts near, or within sites in, the cloning vector.

Primers for initiation of DNA synthesis can be of any length that supports stable hybridization between the primer and a complementary portion of the DNA to be amplified. Generally, this is between about 4 and about 20 nucleotides in length; preferably the primers are hexamers.

Primers used in methods of the invention can contain random or partially random sequences. By primers of "random" sequence is meant that the positions of apposition of the primers to the nucleic acid template are substantially indeterminate with respect to the nucleic acid sequence of the template under the reaction conditions used in the methods of the invention. It is recognized that the sequences of random primers may not be random in the mathematic sense. Chemically synthesized random primers will be random to the extent that physical and chemical efficiencies of the synthetic procedure will allow. Primer types are defined to be random so long as the positions along the template nucleic acid strand at which the primed extensions occur are largely indeterminate, comprising random sequences consisting of permutations of a selected group of nucleotides.

Random primers used in methods of the invention include hexamer primers that contain, at each of the six positions, a random nucleotide selected from A, G, C or T. Alternatively, the nucleotides at each of the six positions may be selected from more limited sets of nucleotides, such as A, G, or C; A, G, or T; A or G; etc. Partially random hexamer primers may have nucleotides at each of the first 5 positions that are selected randomly from a given group of nucleotides (e.g., selected from A, G, C or T; from A, G, or C; from A, G, or T; from A or G; etc.), while the nucleotide at the 3' terminal end of the oligonucleotide is fixed (e.g. either A, G, C or T). In other partially random hexamer primers, the nucleotides at two or three of the six positions may be fixed. Similar distributions of random nucleotides can be present in longer primers, as well. In general, the number of random base positions in the complementary portion of primers are preferably from about 20% to 100% of the total number of nucleotides in the complementary portion of the primers. More preferably the number of random base positions are from about 30% to 100%, or from about 50% to 100%, or from about 85% to 100% of the total number of nucleotides in the complementary portion of the primers.

Among the suitable primers for use in the method of the invention are hexamer primers having the following sequences: HHHHHC (SEQ ID NO:1); DDDDDG (SEQ ID NO:2); VVVVVA (SEQ ID NO:3); BBBBBT (SEQ ID NO:4); HHHHHH (SEQ ID NO:5); RRRRRR (SEQ ID NO:6); YYYYYY (SEQ ID NO:7); NNNNNH (SEQ ID NO:8) NNNNNN (SEQ ID NO:9); MMMMMM (SEQ ID NO:10); KKKKKK (SEQ ID NO:11); SSSSSS (SEQ ID NO:12); or WWWWWW (SEQ ID NO:13). In these formulas, H=A,C, or T; D=A,G, or T; V=A,C, or G; B=C,G, or T; N=A,G,C, or T; R=A or G; Y=C or T; M=A or C; K=G or T; S=C or G; and W=A or Y. Other suitable primers include primers having the following sequences: $(H)_nC$; $(D)_nG$; $(V)_nA$; and $(B)_nT$, wherein n is an integer between 3 and 19, preferably between 4 and 6, and H, D, V and B are as described.

In a preferred embodiment, the primers include modified nucleotides to render them resistant, to exonuclease digestion. For example, 1, 2, 3 or more phosphorothioate linkages may be present. In embodiments of the invention, the two most 3' terminal residues are linked by phosphorothioate linkages; or the three most 3' terminal residues are so linked. Typical examples of such primers include: HHHH*H*C (SEQ ID NO:1), wherein H=A, C or T; DDDD*D*G (SEQ ID NO:2), wherein D=A, G or T; VVVV*V*A (SEQ ID NO:3), wherein V=A, C or G; BBBB*B*T (SEQ ID NO:4), wherein B=C, G or T; and HHHH*H*H (SEQ ID NO:5), wherein H=A, C or T. In each of these primers, * indicates a phosphorothioate linkage. Another preferred primer is NNNN*N*N (SEQ ID NO:9), wherein N=A,G,C or T.

Primers used in methods of the invention can have one or more modified nucleotides. Such primers are referred to herein as modified primers. Modified primers have several advantages. First, some forms of modified primers, such as RNA/2'-O-methyl RNA chimeric primers, have a higher melting temperature (Tm) than DNA primers. This increases the stability of primer hybridization and will increase strand invasion by the primers. This will lead to more efficient priming. Also, since the primers are made of RNA, they will be exonuclease resistant. Such primers, if tagged with minor groove binders at their 5' end, will also have better strand invasion of the template dsDNA.

Chimeric primers can also be used. Chimeric primers are primers having at least two types of nucleotides, such as both deoxyribonucleotides and ribonucleotides, ribonucleotides and modified nucleotides, or two different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. The DNA and RNA portions of such primers can have random or degenerate sequences. Other forms of chimeric primers are, for example, 5'-(2'-O-Methyl)RNA-RNA-3' or 5'-(2'-O-Methyl)RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al. (1991) *Angewandte Chemie, International Edition* 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Primers composed, either in whole or in part, of nucleotides with universal bases are useful for reducing or eliminating amplification bias against repeated sequences in a target sample. This would be useful, for example, where a loss of sequence complexity in the amplified products is undesirable. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[($CH_2$)nO]m $CH_3$, —O($CH_2$)nOCH$_3$, —O($CH_2$)nNH$_2$, —O($CH_2$)nCH$_3$, —O($CH_2$)n-ONH$_2$, and —O($CH_2$)nON[($CH_2$)nCH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$, CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CB$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-allylene phosphonate and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

It is understood that nucleotide analogs need only contain a single modification, but may also contain multiple modifications within one of the moieties or between different moieties.

Nucleotide substitutes are nucleotides or nucleotide analogs that have had the phosphate moiety and/or sugar moieties replaced. Nucleotide substitutes include molecules having similar functional properties to nucleotides, but which do not contain a phosphate moiety, such as peptide nucleic acid (PNA). Nucleotide substitutes include molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate back-bones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules. See also Nielsen et al. (1991) *Science* 254, 1497-1500.

Primers of the invention can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Primers may, but need not, also contain additional sequence at the 5' end of the primer that is not complementary to the target sequence. This sequence is referred to as the non-complementary portion of the primer. The non-complementary portion of the primer, if present, serves to facilitate strand displacement during DNA replication. The non-complementary portion of a primer may be any length, but is generally 1 to 100 nucleotides long, and preferably 4 to 8 nucleotides long.

Sets of primers having random or partially random sequences can be synthesized using conventional techniques by allowing the addition of any nucleotide (or any of a more limited set of nucleotides, as set forth above) at each position to be randomized. It is preferred that the sets of primers are composed of primers of similar length and/or hybridization characteristics. Conventional synthesis techniques include using phosphoroamidite solid-phase chemistry to join nucleotides by phosphodiester linkages. Chemistry for joining nucleotides by phosphorothioate linkages or different linkages, such as methylphosphonate linkages, can also be used. For example, the cyanoethyl phosphoramidite method can be used, employing a Milligen or Beckman System 1 Plus DNA synthesizer (for example, Model 8700 automated synthesizer of Milligen-Biosearch, Burlington, Mass. or ABI Model 380B). Synthetic methods useful for making oligonucleotides are also described by Ikuta et al. (1984) *Ann Rev. Biochem* 53, 323-356, (phosphotriester and phosphite-triester methods), and Narang et al. (1980) *Methods Enzymol.* 65, 610-620 (phosphotriester method). Protein nucleic acid molecules can be made using known methods such as those described by Nielsen et al. (1994) *Bioconjug. Chem.* 5, 3-7. Primers prepared by methods as above are available from commercial sources, such as Integrated DNA Technologies (IDT), Coralville, Iowa.

During amplification, one may additionally include radioactive or modified nucleotides, such as bromodeoxyuridine triphosphate, in order to label the DNA generated in the reaction. Alternatively, one may include suitable precursors that provide a binding moiety such as biotinylated nucleotides.

Generally, the DNA polymerase used to perform MDA, such as rolling circle amplification, is a Φ29-type polymerase. By "Φ29-type" DNA polymerase is meant any DNA polymerase isolated from the related phages which contain a terminal protein used in the initiation of replication of DNA. These phages are generally described by Salas, in The Bacteriophages 169, 1988. These phages are closely related in the structure of their DNA polymerases, some differing by as few as 6 amino acid changes with 5 of those amino acids being replaced by similar amino acids. These phages have a short inverted terminal repeat sequence of length between about 6 and 300 nucleotides. These polymerases have a highly active 3'-5' exonuclease activity, but no 5'-3' exonuclease activity. In preferred embodiments, the 029-type DNA polymerase is chosen from the DNA polymerases of phages: Φ29, Cp-1, PRD1, ΦPRD1, Φ15, Φ21, PZE, PZA, Nf, M2Y, B103, SFS, GA-1, Cp-5, Cp-7, PR4, PRS, PR722, or L17; or the DNA polymerase is a Φ29-type polymerase that has been modified to have less than ten percent (e.g., less than one percent, or substantially none) of the exonuclease activity of the naturally-occurring polymerase.

Preferably, the DNA polymerase is Φ29 DNA polymerase (sometimes referred to herein as Φ29 Pol; Φ29 polymerase; or phi29 polymerase). See, e.g., U.S. Pat. Nos. 5,198,543 and 5,001,050 to Blanco et al. Purified Φ29 Pol is available commercially, e.g. from New England Biolabs. Φ29 polymerase has been shown to amplify circular DNA isothermally at 30° C., by a highly processive rolling circle mechanism (Lizardi et al. (1998) *Nat Genet.* 19, 225-32; Dean et al. (2001) *Genome Res.* 11, 1095-9). It has been reported that the average size of these elongation products is about 70 kb; other reports suggest that Φ29 polymerase can synthesize products as long as about 650,000 nt (cited in Dean et al. (2001), supra) or potentially as long as 1,000,000 nt (cited in Nelson (2002) *Journal of Clinical Ligand Assay* 25, 276-279). When primed by a set of random primers, the synthesis produces products from multiple priming sites on each original template molecule. These products can also serve as templates for additional synthesis, resulting in complex branched pinwheel structures, which comprise double-stranded DNA. This type of structure is illustrated in FIG. 1. The reaction goes through an exponential phase, so it potentially can have a sensitivity similar to, or greater than, PCR. Phi29 polymerase has been reported to have an error rate of only 1 in $10^6$-$10^7$ bases, and to exhibit a much higher fidelity than the polymerases used for PCR (Esteban et al. (1993) *J Biol Chem* 268(4), 2719-26). Consequently, the error rate in molecules cloned by Φ29 polymerase amplification is expected to be low. See Example X for a further discussion of the Φ29 polymerase error rates and the accuracy of Φ29 cloning.

Other DNA polymerases are also suitable for use in methods of the invention, provided that they exhibit processive, strand-displacing activity and can, e.g., perform rolling circle replication of primed single-stranded circles. Such DNA polymerases are sometimes referred to herein as "strand displacement" polymerases or "rolling circle" polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the circular vector. A 5' to 3' exonuclease activity, if present, might result in the destruction of the synthesized strand. It is also preferred that DNA polymerases for use in the disclosed method are highly processive, copy DNA with high fidelity, and/or comprise a proofreading activity (a 3' editing function). The term "processive," as used herein, means that the DNA polymerase remains attached to the elongation complex without dissociating, thereby allowing the elongation of very long DNAs. The suitability of a DNA polymerase for use in the disclosed method can be readily determined by assessing its ability to carry out MDA (e.g. rolling circle replication). Among the suitable DNA polymerases are phage M2 DNA polymerase (Matsumoto et al. (1989) *Gene* 84, 247); VENT™ DNA polymerase (Kong et al. (1993) *J Biol. Chem.* 268, 1965-1975); Klenow fragment of DNA polymerase I (Jacobsen et al. (1974) *Eur. J. Biochem.* 45, 623-627); T5 DNA polymerase (Chatteijee et al. (1991) *Gene* 97, 13-19); modified T7 DNA polymerase (Tabor et al. (1987) *J Biol Chem.* 262, 15330-15333; Tabor et al. (1989) *J Biol Chem.* 264, 6447-6458); Sequenase™ (U.S. Biochemicals); and T4 DNA polymerase holoenzyme (Kaboord et al. (1995) Curr. Biol. 5, 149-157).

If necessary, strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include BMRF1 polymerase accessory subunit (Tsurumi et al. (1993) *J. Virology* 67, 7648-7653); adenovirus DNA-binding protein (Zijderveld et al. (1994) *J. Virology* 68, 1158-1164); herpes simplex viral protein ICP8 (Boehmer et al. (1993) *J. Virology* 67, 711-715; Skaliter et al. (1994) *Proc. Natl. Acad. Sci. USA* 91, 10665-10669); single-stranded DNA binding proteins (SSB; Rigler et al. (1995) *J. Biol. Chem.* 270, 8910-8919); and calf thymus helicase (Siegel et al. (1992) *J. Biol Chem.* 267, 13629-13635).

The ability of a polymerase to carry out MDA (e.g. rolling circle replication) can be determined by using the polymerase in a conventional assay, such as the rolling circle replication assay described herein or in Fire et al. (1995) *Proc. Natl. Acad. Sci. USA* 92, 4641-4645.

It is possible to enhance the specificity of the DNA amplification reactions used in the disclosed method by using a DNA polymerase that is inactive at low temperature, and active only at high temperature. An example of such an enzyme, AmpliTaq Gold, has been described by Moretti et al. (1998) *Biotechniques* 25, 716-722. AmpliTaq Gold is inactive until heated during the PCR before thermal cycling. A similar enzyme could be used in the disclosed method. Temperature activation of DNA polymerase can also be achieved using antibodies specific for the polymerase. For example, antibodies specific for Bst large fragment DNA polymerase could be obtained by immunization of mice. Among such antibodies, one could be chosen on the basis of its ability to bind to and inhibit the enzyme at room temperature. The antibody could also be chosen, using known screening procedures, such that upon heating, the inhibition of the DNA polymerase would cease. Combining the antibody with Bst large fragment DNA polymerase would generate an enzyme mixture that is activated upon heating.

Amplification/cell-free cloning methods of the invention can be applied to a variety of uses. The inventive method can be used to prepare amplified nucleic acid that can be used, without further purification, for any purpose and in any manner that nucleic acid cloned or amplified by known methods (e.g. in vivo methods) can be used. For example, the nucleic acid can be probed, subcloned, transcribed, further amplified, stored, or be subjected to hybridization, denaturation, restriction, haplotyping or microsatellite analysis or to a variety of SNP typing techniques. Diagnostic uses, such as sequencing and probing for specific sequences, are also included. The inventive methods can also be applied to the uses discussed in DNA Amplification: Current Technologies and Applications, eds Demidov et. al., Horizon Bioscience, 2004.

One aspect of the invention is a method of cell free cloning of a DNA of interest, comprising amplifying a single copy of the DNA of interest by an RCA method of the invention. For example, a pool of DNA molecules of interest may be subjected to limit dilution (end point dilution), such that the samples contain, on average, one molecule of DNA. That is, some samples contain one DNA molecule, others two, and others none. The DNA molecules in each sample are then converted to single-stranded circles, if necessary, and amplified by a method of the invention. In one embodiment, a dsDNA molecule is circularized and, optionally, converted to ssDNA before the limit dilution step is performed. Samples in which a single copy of the template DNA was present are selected. A single copy of a DNA of interest can thus be cloned by an in vitro method, without ever being subjected to an in vivo cloning procedure (e.g. growth/passage through living cells, such as bacteria). The ability to generate copies of large DNAs (e.g. about 7,000 to about 500,000 nt) by the method allows the cloning of large DNAs.

Another aspect of the invention is a method for assembling a gene or genome, e.g. a mitochondrial genome or a minimal genome, such as from a mycoplasma, that encodes all of the machinery for independent life. The method comprises one or more of the steps of amplifying (cloning) portions of the gene or genome by a method of the invention; sequencing the cloned DNAs; correcting errors, if any, in the amplified sequences; and assembling the amplified DNAs to form the gene or genome. In one embodiment, the DNA portions are prepared by synthetic methods.

As used herein, the singular forms "a," "an," and "the" include plural referents unless the context clearly dictates otherwise. For example, "a" synthetic gene, as used above, includes two or more synthetic genes.

Another aspect of the invention is a method for sequencing a DNA of interest, e.g. for a genomic sequencing project, comprising amplifying the DNA to be sequenced by a method of the invention, and sequencing the amplified DNA. In this method, the template DNA or the amplified DNA does not pass through a step of in vivo cloning. The method can substantially reduce the time required for preparation and sequencing of templates; leads to a reduction in problems with otherwise unclonable sequences; and can be readily adapted to high throughput methods which can be automated and performed robotically. The nucleotide sequence of the amplified DNA can be determined by conventional means, such as conventional Sanger sequencing, e.g. using an ABI capillary sequencer from Applied Biosciences (Foster City, Calif.). Various forms of primer extension sequencing can be employed. One form of sequencing for use with amplified sequences produced with the disclosed method is nanosequencing or single-nucleotide extension sequencing. Single nucleotide primer extension sequencing involves interrogation of a single nucleotide in an amplified target sequence by incorporation of a specific and identifiable nucleotide based on the identity of the interrogated nucleotide. Degenerate probe primer extension sequencing involves sequential addition of degenerate probes to an interrogation primer hybridized to amplified target sequences. Suitable sequencing methods are described, e.g., by Jalanko et al. (1994) *Clinical Chemistry* 38, 39-43 (1992); Nikiforov et al. (1994) *Nucleic Acids Research* 22, 4167-4175; Kobayashi et al. (1995) *Molecular and Cellular Probes* 9, 175-182; and in PCT Application WO 97/20948.

Furthermore, mate-paired sequence reads from the ends of clones generated by a method of the invention (e.g., Φ29 polymerase cell-free clones) can facilitate the assembly of data generated by a new generation of sequencers such as the 454 Genome Sequencer 20 (454 Life Sciences, Roche Applied Sciences) (Margulies et al. (2005) *Nature* 437, 376-80; Rogers et al. (2005) *Nature* 437, 326-7). Such devices have extremely high throughput and do not rely on *E. coli* cloning, but currently produce only short read lengths of lower quality than conventional methods. Combining such "454 data" with cell-free clone data (e.g., Φ29 polymerase cell-free clone data) results in an extremely rapid and accurate genome sequencing method.

Another aspect of the invention is a method for amplifying a single copy of a DNA template by a cell-free method of the invention, using an automated nanomolar system. The method comprises combining in a reaction chamber, such as a glass capillary tube, preferably in a volume of about 200 nl or less (e.g., a volume of about 64 nl or less), a reaction mixture comprising the DNA template, a DNA polymerase, and a mixture of suitable primers; and incubating the reaction mixture under conditions that are effective for promoting DNA strand displacement, at a substantially isothermal temperature.

In one embodiment of this method, the amplification reactions are carried out in an automated nanoliter system, such as the Parallab 350 machine manufactured by Brooks Automation Inc., 15 Elizabeth Drive, Chelmsford, Mass., 01824, USA. A desirable system processes many reactions (e.g. about 50, 96, 500, 1,000 or more reactions) in parallel; aspirates, mixes, thermal cycles (if desired) and purifies components inside of miniature glass tubes (capillaries); uses a standard reaction size of 500 nl, although this can be readily reduced to 200 nl or as little as 64 nl; and uses small amounts, such as 190 nl, of a marker such as Big Dye®. Other desirable properties of an automated nanoliter system include the ability to automatically decontaminate for reuse without the need for disposable tips; to produce liquid handling accuracies of <5% Cv at 200 nl; and to be designed for easy field maintenance.

Using a device such as a Parallab 350 nanoliter genomic workstation, DNA amplification can be carried out in an unattended automated system. Reaction components and associated isolation and cleanup materials can be stored together. To begin a reaction, a robot may move to the required location and remove a lid to provide access for a nanoliter liquid handler such as the Nano-Pipetter available from Parallab. For example, the liquid handler may withdraw reagent into 96 thin-walled 500 nl glass capillaries, each serving as a reaction vessel. The components can be mixed by high speed shuttling of the fluids inside the capillaries. Following the reaction, optionally magnetic bead solution can be aspirated into each reaction tube to isolate the amplified DNA. Accordingly, as many as 96 DNA products can be dispensed into an output plate for off-line analysis. The nanoliter liquid handler can be automatically cleaned with an onboard wash station in preparation for another reaction run.

Other automatic (robotic) systems can also be used, such as various high throughput, nanomolar devices, including those which employ microfluidic methods, examples of which are known to skilled workers. Some such devices include: the closed-cycle capillary PCR machine described in Chiou et al. (2001) *Anal. Chem.* 73, 2018-21; the Roche capillary thermocycler (LightCycler™) described in Tan et al. (2004) *Expert Reviews of Molecular Diagnosis* 4, 219-230; the miniaturized assembly for detecting the presence of a single target nucleic acid in a sample in U.S. patent application 2004/0171055; and the microcapillary PCR device described with regard to a nanoscale scale PCR method in Kalinina et al. (1997) *Nuc. Acids Research* 25, 1999.

Alternatively, multiple amplification reactions can be carried out in parallel in arrays, on beads, or as spreads of diluted vectors on surfaces or embedded in agarose. The resulting "colonies" of amplified DNA represent molecular clones of the progenitor circular vectors with an inserted nucleic acid molecule. Collectively, such colonies form a library of cloned nucleic acid molecules that can be replica plated or arrayed, stored, and screened. Typical such procedures are described in U.S. Pat. No. 6,287,824 to Lizardi.

As noted, the yield of DNA amplified by a method of the invention in a single reaction chamber (e.g. in a single round of replication) can be an amplification of at least about $2 \times 10^8$ fold, e.g. about $5 \times 10^8$ fold, $10^9$ fold, $2 \times 10^9$ fold, $5 \times 10^9$ fold, $10^{10}$ fold, $2 \times 10^{10}$ fold, or greater of the starting material. A variety of suitable reaction chambers will be evident to a skilled worker. These include, e.g., a tube (such as a capillary tube), droplet, vial, capsule, ampule, or other vessel. A tube can have a removable cap and/or a replaceable cap. The cap can maintain the container sealed such that the container is water-tight and air-tight. The container can be hermetically sealed. The container can be open at a first end and closed at a second end. According to various embodiments, the first end can be tapered, for example, along the length of the container. According to various embodiments, the container can hold a mixture including assay reagents and have a volume of, for example, equal to or less than about 10 µl (e.g. 1 µl or less, 0.064 µl or less, or even smaller).

In one embodiment of the invention, the yield of amplified product is extended by, following a suitable period of incubation and amplification, determining the presence of amplified nucleic acid in an amplification reaction and transferring an aliquot of that first amplification reaction containing amplified nucleic acid to a fresh set of reaction mixtures. The fresh reaction mixture into which an aliquot is diluted will contain polymerase, nucleotides to replenish the depleted nucleotide pools from the previous reaction, and salts, etc. required for further amplification. In one embodiment, the fresh reaction mixture contains a set of primers which are the same as those used in the first amplification. In another embodiment, in order to reduce further amplification of built-up sequence units that may have contributed to background synthesis in the first reaction, a different set of partially random or defined primers is used, which would not be expected to interact with primers from the first reaction mix. If desired, residual primers remaining from the first reaction mix can be removed, e.g. by enzymatic means. The fresh reaction mix, containing amplified DNA from the first reaction mixture, is then incubated under conditions that are effective for promoting DNA strand displacement, at a substantially isothermal temperature.

Any combination of the materials useful in the disclosed methods can be packaged together as a kit for performing any of the disclosed methods. Vectors and primers are useful components of such kits. Enzymes necessary for the disclosed methods can also be components of such kits. A skilled worker will recognize components of kits suitable for carrying out any of the methods of the invention. Optionally, the kits comprise instructions for performing the method. Kits of the invention may further comprise a support or matrix to which elements of the invention can be attached or immobilized. Other optional elements of a kit of the invention include suitable buffers, or the like, containers, or packaging materials. The reagents of the kit may be in containers in which the reagents are stable, e.g., in lyophilized form or stabilized liquids. The reagents may also be in single use form, e.g., in a form for a single amplification.

In one embodiment, the kit comprises, e.g., a set of primers, such as a set of defined primers, and/or a set of hexamer primers whose sequence is represented by SEQ ID NO:1 or SEQ ID NO:5; and/or a set of hexamer primers represented by the formula HHHH*H*C (SEQ ID NO:1), or by the formula HHHH*H*H (SEQ ID NO:5), wherein H=A,C or T, and * indicates a phosphorothioate linkage. The primers in the kit may be packaged at a concentration suitable for a single amplification reaction, or they may be present in an amount suitable for multiple amplification reactions. In one embodiment, the kit comprises a multipurpose vector of the invention.

In the foregoing and in the following examples, all temperatures are set forth in uncorrected degrees Celsius; and, unless otherwise indicated, all parts and percentages are by weight.

EXAMPLES

Example I

Material and Methods

DNA preparations. ΦX174 am3cs70 single-stranded virion DNA, and M13 mp18 single-stranded DNA were obtained from New England BioLabs (NEB, Beverly, Mass.). The DNA referred to as syn ΦX in the text was the ligated circular double-stranded synthetic ΦX174 DNA described by Smith et al. (2003) *Proc. Natl. Acad. Sci. USA* 100, 15440-445. The *M. genitalium* genomic DNA library was prepared from DNA isolated from strain G37, obtained from the ATCC in 1996. DNA sheared to 1.5-2.2 kb was cloned into a medium copy pBR322 derivative as described previously (Adams et al. (2000) *Science* 287, 2185-95).

Enzymes. Φ29 DNA polymerase was purchased from NEB in pure form at a concentration of 10,000 units/ml. Inorganic pyrophosphatase from USB Corporation was supplied at 40 units/ml. Restriction enzymes were from NEB.

Φ29 polymerase amplification reactions. Reactions contain 37 mM Tris-HCl (pH7.5), 50 mM KCl, 10 mM $MgCl_2$, 5 mM $(NH_4)_2SO_4$, 1 mM each of the four dNTPs, 1 mM DTT, 1×BSA (NEB), 0.2% Tween 20, 1 unit/ml yeast pyrophosphatase, 540 units/ml Φ29 DNA polymerase, and 50 μM exonuclease-resistant hexamer mix (Fidelity Systems, Inc., Gaithersburg, Md.). All components except the enzymes and hexamers were made up as a 2× concentrated buffer (2×G-buffer). Immediately before setting up reactions, enzymes and $H_2O$ were added to 2×G-buffer, this was incubated 10 min at room temperature, and the hexamers were added so that the concentration of all components was now 1.5× the final reaction conditions (this is Φ29 Mix). Reactions were initiated by adding one volume of template DNA in TE buffer to two volumes of Φ29 Mix. Reactions were carried out at 30 C. For our standard 600 nl reaction 400 nl of Φ29 Mix was added to a 0.5 ml PCR tube using a 2 μl Pipetman (Gilson, Inc., Middleton, Wis.). Then 200 nl of template dilution was added and the reaction was mixed by pipeting up and down about 20 times. Reactions were overlaid with 10 μl of Bio-Technology Grade mineral oil (Bio-Rad Laboratories, Hercules, Calif.) to prevent evaporation, then centrifuged briefly and checked visually to make sure the aqueous phase forms a small sphere at the bottom of the tube. Reactions were incubated in a thermocycler at 30 C. for 6 hrs, then held at 4 C. until analysis.

PCR was carried out in Advantage 2 buffer, using the Advantage HF 2 PCR Kit (catalog no. K1914-1, Clontech Laboratories, Mountain View, Calif.).

Restriction analysis of amplification reactions. To digest the entire reaction 20 μl of NEB buffer 2 plus BSA (1×, NEB) containing 10 units of Pst I was added to the reaction under mineral oil, the tube was mixed briefly and incubated at 37 C. for 30-60 min. The aqueous phase was removed and loaded onto an E-Gel (Invitrogen Corporation, Carlsbad, Calif.). Unless stated otherwise, 0.8% E-Gels were electrophoresed at for 40 min. at 60 V. DNA size markers were HyperLadder I (Bioline USA, Randolph, Mass.). To analyze Φ29 polymerase reactions by restriction digestion and also by DNA sequencing, the reactions were diluted with 10 μl of TE and then split for analysis.

DNA sequencing. PCR and Φ29 polymerase reaction products were treated with shrimp alkaline phosphatase (SAP) and *E. coli* exonuclease I (Exo I) to remove primers and dNTPs before use as sequencing templates. SAP-Exo I master mix contained 0.5 μl SAP (Boerhinger Mannheim, Germany, 1 unit/μl), 0.1 μl Exo I (NEB, 20 units/μl), 0.5 ml 10×SAP buffer and 8.9 μl $H_2O$ per reaction. To sequence from a PCR reaction 8 μl of the reaction was added to 10 μl of SAP-Exo I master mix and the solution was incubated at 37 C. for 60 min, then at 72 C. for 15 min, and then held at 4 C. until use in sequencing. To sequence directly from a Φ29 polymerase reaction the 600 nl reaction was diluted with 10 ml of TE. 4 μl of the reaction was added to 5 μl of SAP-Exo I master mix and the solution was incubated as for the PCR samples above. In either case 4 μl of the treated templates were sequenced in 8 μl reactions using big dye terminator chemistry (version 3.1, Applied Biosystems, Foster City, Calif.) with 35 extension cycles of 4 min at 60 C. DNA sequencing was carried out using an ABI model 3100 capillary sequencer equipped with 50 cm capillaries.

Example II

Figure 2:
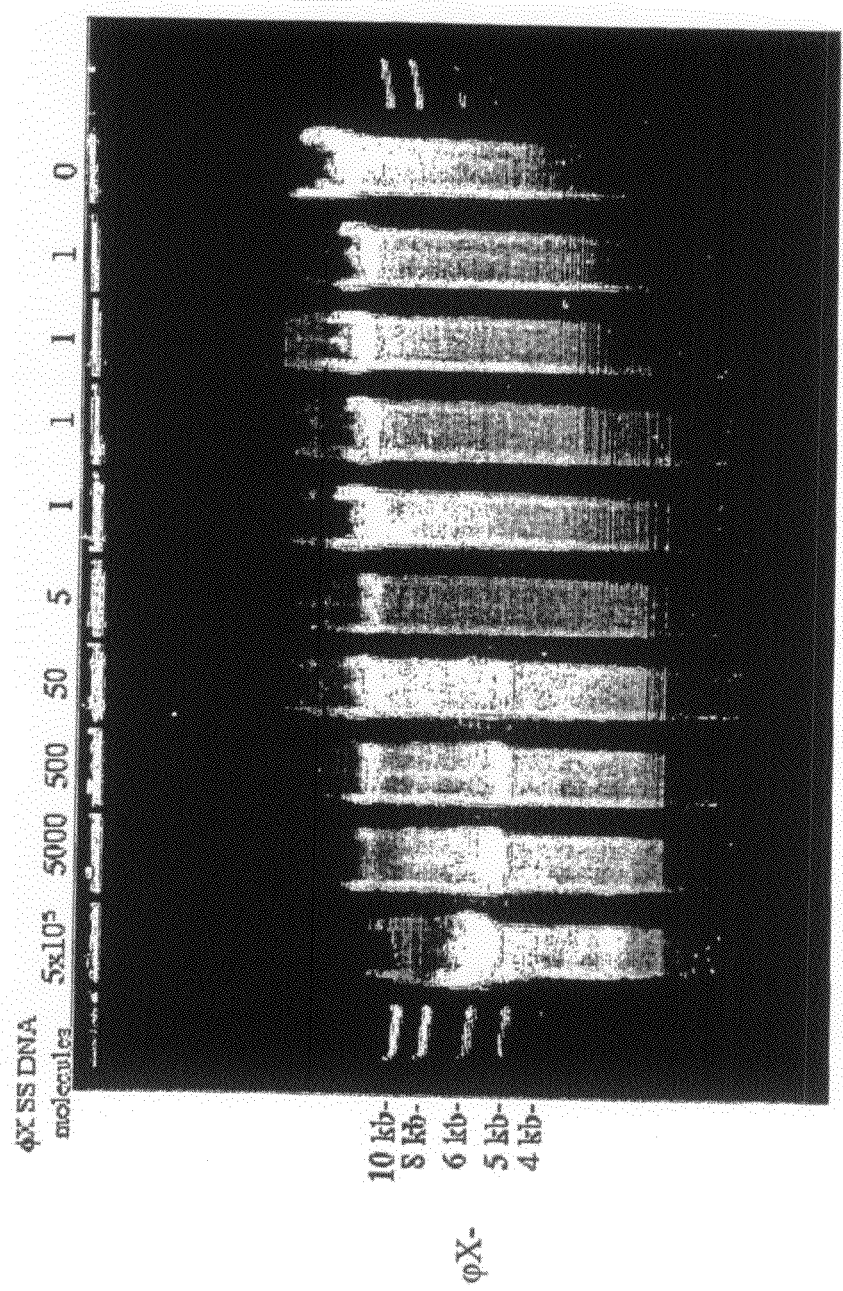
FIG. 2 shows that background synthesis increases with decreasing template. 3 µl φ29 polymerase reactions were primed by the indicated numbers of φX single-stranded DNA molecules, calculated on the basis of dilution factors from a stock of known concentration. Reactions were digested with Pst I and analyzed by gel electrophoresis.

Background Synthesis Increases with Decreasing Amount of Template, and Signal to Background Ratio Improves for Small Reactions As the amount of template DNA in a Φ29 polymerase rolling-circle amplification reaction is decreased, the amount of background synthesis increases. If the template is circular ΦX174 single-stranded DNA (FIG. 2) then Pst I cleaves authentic amplification product at the unique site to produce 5.4 kb linear DNA. The background product, however, does not in general contain Pst I sites and migrates as large DNA, making it easy to distinguish from the rolling-circle amplification product of ΦX174 (FIG. 2).

As the reaction volume is decreased, keeping the amount of template DNA constant, background is dramatically decreased with a marked improvement in signal to noise ratio (FIG. 3A). Using 50 molecules of single-stranded M13 DNA (7.2 kb) as template, a Pst I digest of a 3 μl of a Φ29 polymerase reaction displayed a clear band (>10 ng) of M13 linear. When template was omitted from the reaction a similar amount of DNA was produced by background synthesis, but this DNA was not cleaved by Pst I. Larger reactions (15 μl and 30 μl) produced so much background synthesis that no M13 product was visible. FIG. 3B shows that a reduction to a volume of 0.6 μl results in even further reductions in background.

Example III

End Point Dilution and Cell-Free Cloning of Single Molecules

Figure 4:
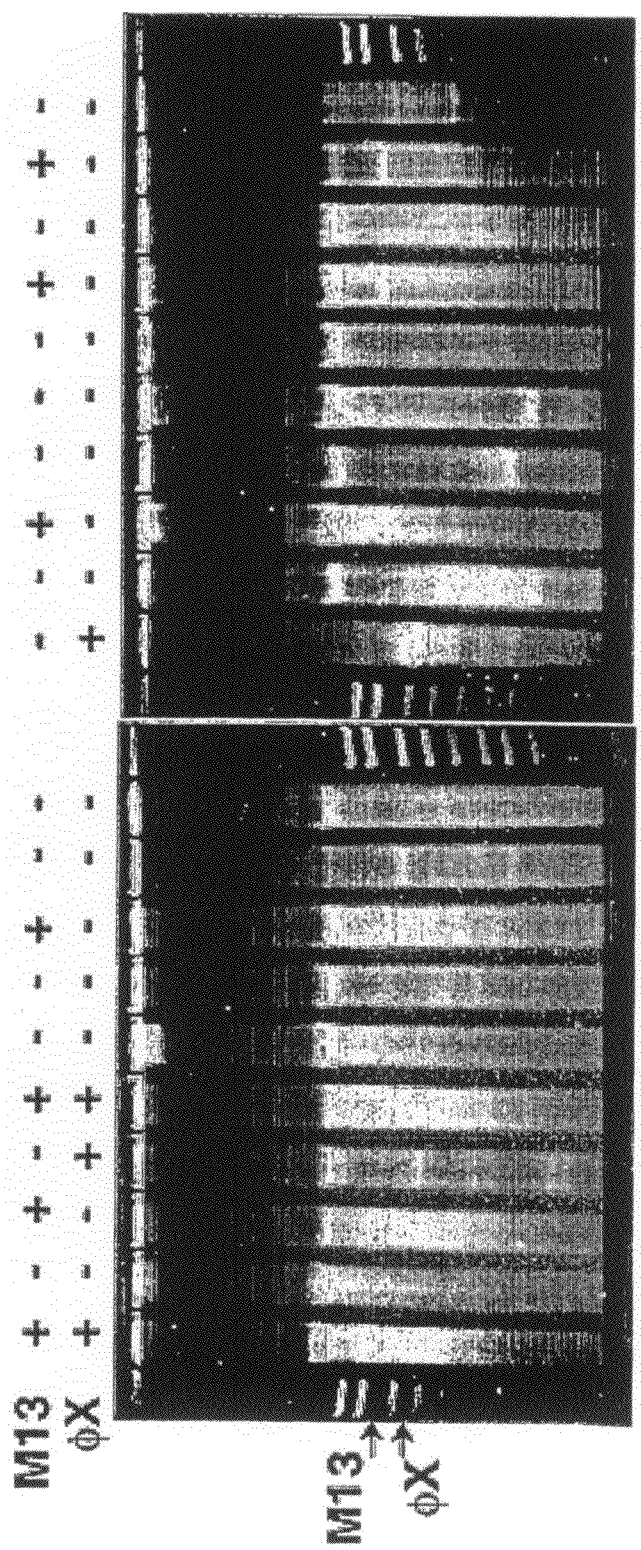
FIG. 4 shows cell-free cloning of φX174 and M13 from a mixture. Twenty duplicate 600 nl φ29 polymerase reactions were made using the same dilution of a mixture of φX174 and M13 DNAs. The reaction products were digested with Pst I and analyzed by gel electrophoresis.

Using 600 nl φ29 polymerase reactions, we have amplified single molecules more than $10^9$-fold to give 10 ng or more of product DNA, allowing easy visualization by ethidium bromide staining following gel electrophoresis. FIG. 4 displays gel electrophoresis of twenty duplicate 600 nl φ29 polymerase reactions digested with Pst I. The template for each reaction was 200 nl of the same diluted mixture of φX174 (5.4 kb) and M13 (7.2 kb) single-stranded DNAs, each of which contains a unique Pst I site. Some lanes appear to contain neither φX nor M13 (11/20), some φX only (2/20), some M13 only (5/20), and some both (2/20). Cloning of φX174 and M13 from a mixture has been confirmed by PCR and real-time PCR analysis of reactions like those shown in FIG. 4, demonstrating that some reactions are positive for each of the molecules but completely negative for the other (data not shown). Some lanes in FIG. 4 display bands that are not the correct size for either φX174 or M13. This phenomenon is often seen in reactions to which no template is added, and we believe it results from the chance occurrence of Pst I sites in the products of background synthesis. The template aliquots used in the reactions of FIG. 4 were estimated to contain an average of 4 φX174 molecules and 2 M13 molecules based upon UV absorbance of the starting DNA samples before dilution. The fraction of molecules participating in the amplification reaction varies somewhat from one dilution series to another, but is fairly constant from day to day for the same DNA dilutions. Variability may result, in part, from adherence of molecules to tubes, pipets, or particulate material, when the DNA concentration is very low.

Example IV

Cloning of Double-Stranded Circular DNA

Figure 5:
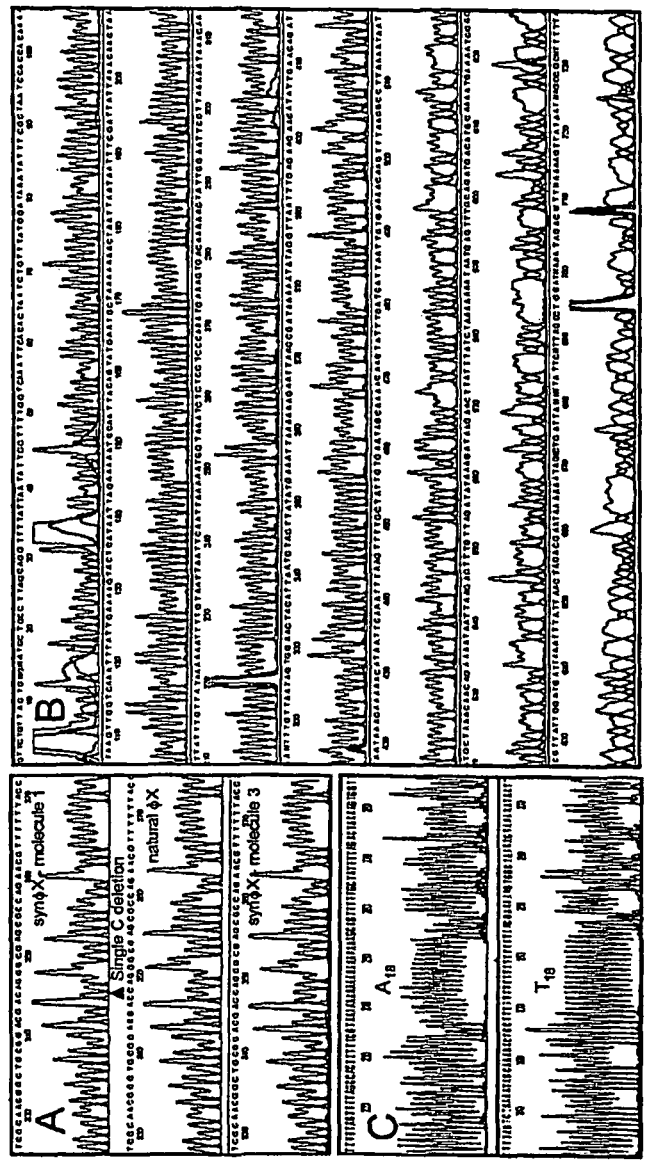
FIGS. 5A, 5B and 5C show DNA sequencing of φ29 polymerase clones.

We also succeeded in cell-free cloning of double-stranded circular DNA. The synthetic φX174 genome preparation that we described previously (Smith et al. (2003), supra) was heated to 95 C. and then quick-cooled to 0 C., to promote priming by random hexamers. About 1 in $10^4$ molecules in this preparation is an infectious phage genome, leading to an estimate of approximately 10 lethal mutations per molecule (Smith et al. (2003), supra). FIG. 5A shows a portion of the sequencing chromatograms from two molecules cloned by φ29 polymerase amplification. For comparison we also sequenced a commercial preparation of natural φX174 DNA. We sequenced about 1 kb from 7 different molecules. Each had a distinct set of sequence differences from the natural DNA preparation. As an example, FIG. 5A displays a deletion of a single nucleotide (C) in molecule 1. Molecule 3 and the natural DNA both have the wild-type sequence at that position as do the other 5 molecules sequenced (not shown). The sequence reads for the cell-free φX174 clones are accurate to beyond 700 bp (see supporting information).

Example V

Making a Library for Φ29 Cloning

Figure 6:
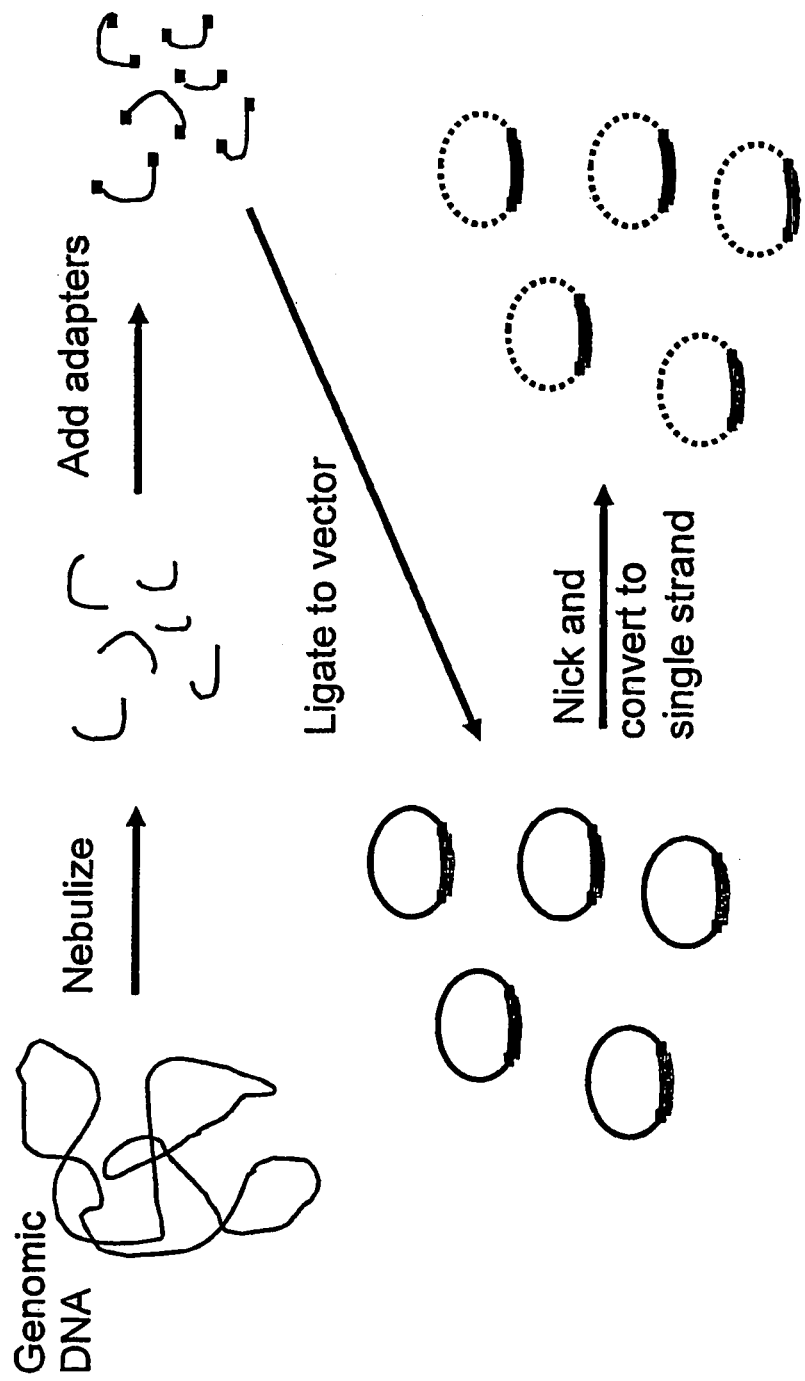
FIG. 6 shows schematically how to construct a genomic library for Φ29 cloning.

FIG. 6 illustrates schematically a method for Φ29 cloning of a genomic library. Genomic DNA is fragmented (e.g. by nebulizing) to fragments of about 5 kb, and adaptors are added to the ends of the fragments, ligated to vectors, nicked, and converted to single-stranded DNA circles. The circles are then amplified by rolling circle by the methods of the invention.

Example VI

Cell Free Cloning of Bacterial Genomic DNA with Φ29 Polymerase Reactions

Figure 7:
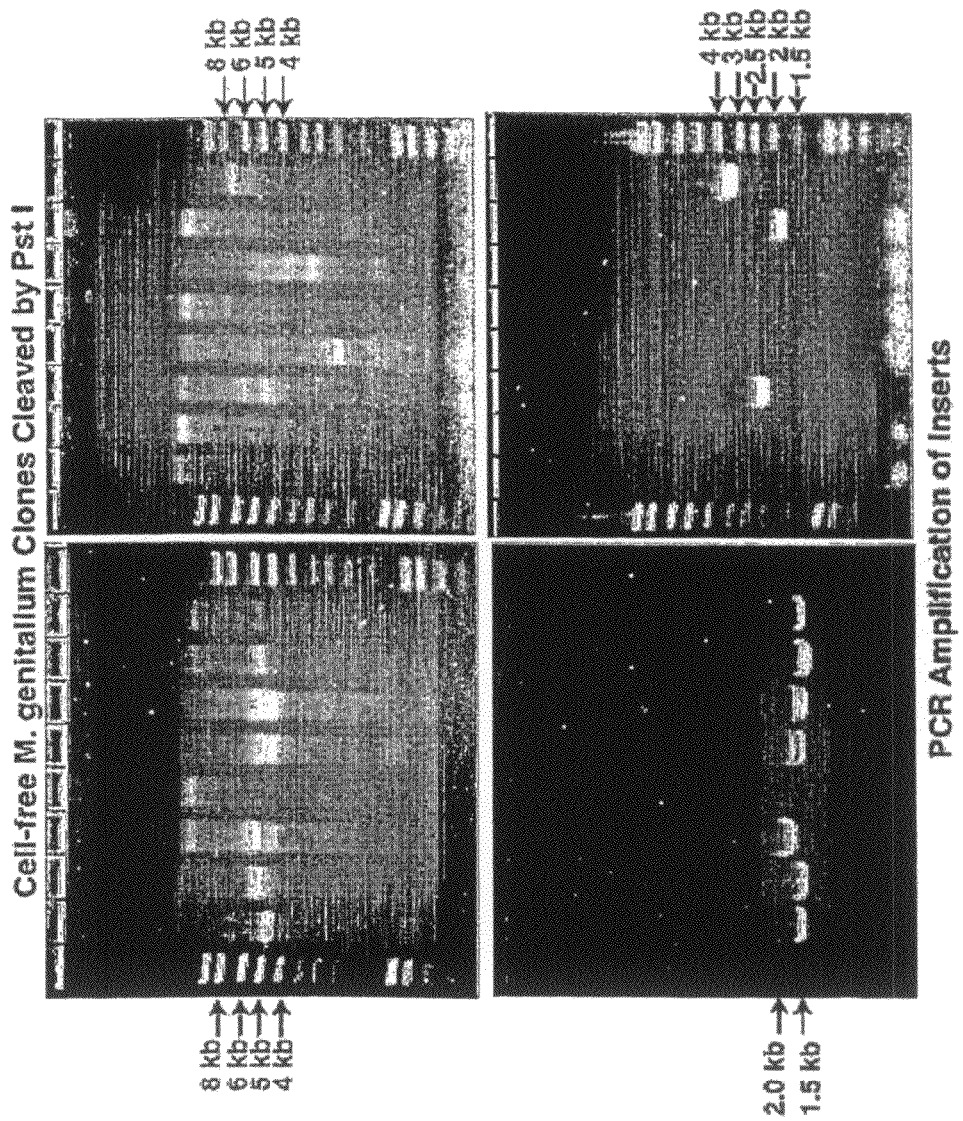
FIG. 7 shows cell-free cloning of *M. genitalium* genomic DNA. A library consisting of 1.5 to 2.5 kb fragments of *M. genitalium* DNA ligated to a pBR322 derivative was diluted 100-fold in TE from an initial DNA concentration of ~0.3 ng/µl, heated at 95° C. for 2 min, then quenched on ice. The DNA was diluted an additional 1000-fold (upper left gel) or 2000-fold (upper right gel) and used as template in two sets of 600 nl φ29 polymerase reactions (8 duplicate reactions per set). Half of each reaction was cleaved with Pst I and analyzed by gel electrophoresis (upper gels). Inserts were amplified by PCR from the remaining portion of each reaction, using M13 forward and reverse sequencing primers that flank the cloning site in the vector, and analyzed on the lower gels.

We cloned segments of bacterial genomic DNA in 600 nl φ29 polymerase reactions. We started with a library of *M. genitalium* genomic DNA sheared to about 2 kb and ligated into the conventional sequencing vector pBR194c. It should be noted that this *M. genitalium* DNA was never propagated in *E. coli*. The library DNA was diluted to give φ29 polymerase reactions primed by individual molecules. FIG. 7 (upper panels) shows the analysis of such reactions cleaved with Pst I. Because the vector is 3.5 kb in size we expect the clones to have a total size of about 5.5 kb. Most positive lanes in FIG. 7 have a band in this size range but the sizes vary somewhat, as would be expected because the cloned DNA was not perfectly homogeneous in size. The inserts were amplified by PCR using the M13 forward and reverse sequencing primer sites that flank the cloning sites in the vector (FIG. 7, lower panels). Some lanes appear to contain two clones of slightly different sizes. PCR products that appeared on the gel to be pure species were sequenced from both ends using the M13 sequencing primers. Six of seven cloned molecules gave clearly readable sequence that matched the *M. genitalium* genome sequence perfectly throughout the readable range (out to ~650 bp or greater—see supporting information). The products of 600 nl φ29 polymerase reactions can also be sequenced directly, without PCR amplification. The chromatogram for such a sequence is shown in FIG. 5B, which displays a sequence that matches the *M. genitalium* genome accurately to beyond 750 bp.

Molecules cloned by φ29 polymerase give accurate DNA sequences. However, DNA sequencing determines the consensus sequence, and so does not detect random mutations that might occur during amplification. It is of interest to try to estimate the mutation frequency in the φ29 product amplified from a single molecule. However, this analysis is not straightforward because rolling-circle amplification is not a simple doubling process. Consequently the usual equation relating polymerase error rate, mutation frequency, and number of doublings does not apply. Because many copies are made directly from the original input molecule, jackpots of mutants should not be a problem as they are with mutations arising during the first cycles of a PCR reaction. The φ29 polymerase appears to have an accuracy comparable to other polymerases with a 3' editing, function (Esteban et al. (1993), supra). Calculations based on published estimates of the φ29 polymerase error rate, and reasonable models of the reaction, indicate that the majority of molecules resulting from $10^9$-fold amplification of a 5 kb circular DNA by φ29 polymerase should have exactly the same sequence as the parental molecule.

Example VII

Accurate Amplification of Homopolymer Tracts from Single Molecules

The high processivity of φ29 polymerase allows accurate amplification of homopolymer tracts from single molecules. DNA from an *M. genitalium* clone containing an $A_{18}/T_{18}$ tract was diluted and used to prime single-molecule φ29 polymerase reactions. The DNA from these reactions was sequenced directly and portions of the chromatograms are shown in FIG. 5C. One strand shows a run of 18 A residues, and the complementary strand shows 18 T residues as expected. The sequence is clearly readable beyond the homopolymer run on both strands, and matches the *M. genitalium* genome sequence accurately for the readable length of the run (>700 bp).

Example VIII

Restricted Hexamer Sets of the Invention can Reduce Φ29 Pol Background

Figure 8:
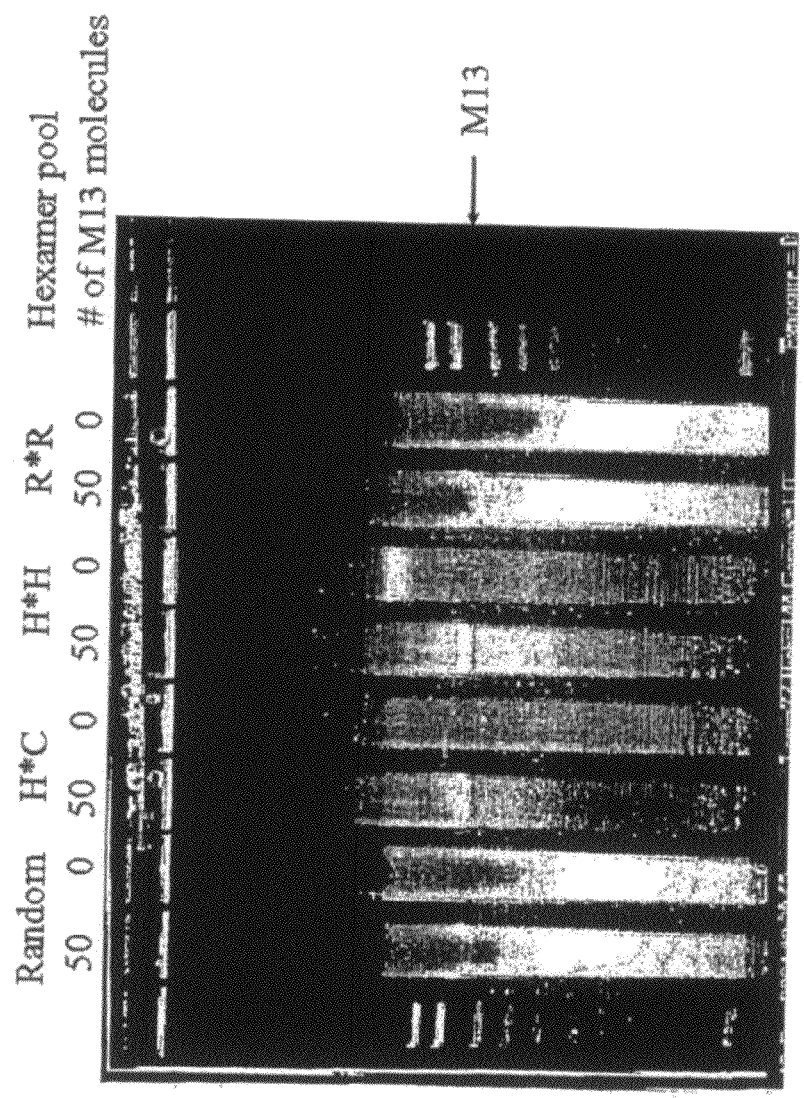
FIG. 8 shows that hexamer sets H*C and H*H can reduce the background synthesis.

FIG. 8 shows that the hexamer primer sets H*C and H*H provide dramatically reduced background compared to a random primer. H*C is a mixture of the $3^5$ (243) sequences HHHHHC (SEQ ID NO:1), where H=A, C, or T. Primer set H*H is a mixture of the $3^6$ (729) sequences HHHHHH (SEQ ID NO:5), where H is as above.

Example IX

A Short Vector Sequence for Inserting Pieces of DNA for Single Molecule Cloning Using the Phi29 Polymerase Amplification System of the Invention To clone a DNA molecule, it is ligated to BstXI adapters and then ligated to the complementary BstXI ends of the vector. The vector is made ready for inserts by cleaving it with BstXI and gel purifying the resulting 196 bp vector fragment. The sequence of the vector and its component sites are shown in FIG. 9. The complementary top and bottom strands of the sequence are identified as SEQ ID NO:14 and SEQ ID NO:15, as indicated. An M13 origin of replication (ori) site allows one strand of the DNA to be nicked and removed, leaving a single-stranded circle for amplification by phi29 polymerase. M13 primer sites allow sequencing into either end of a DNA insert. (The M13 and f1 ori sites are identical.) Two homing endonuclease sites, PI-PspI and I-SceI, permit linearization of the cloned DNA from within the vector sequence. A Lac repressor site is included as a means of specifically binding the vector, using Lac repressor protein, for recovery from mixtures of DNA. BbvCI is an additional nicking site for either strand.

We have developed novel BstXI adaptors that are added to the ends of the DNAs to be cloned. These adaptors contain Type IIS restriction sites, such that the DNA inserts can be excised from the vector without including sequences on the ends that were not present in the cloned DNA. Two possible adapters are shown in Table 1 below. The standard adapter is labeled BstXI adapter and the Type IIS site (leftmost 6 base pairs) is labeled with the enzyme name from New England Biolabs (NEB). When either of these adapters is ligated to the ends of the blunt-ended insert DNA and the DNA is ligated into the vector using the BstXI overlaps, the Type IIS sites will be directly adjacent to the insert DNA and cleavage will occur a short distance into the insert. The loss of a few bases from the ends of the inserts will not affect subsequent assembly reactions. There are at least a dozen other 6-base Type IIS cleavage sites that can be used in addition to the two shown. For any given insert, an adapter can be chosen such that the Type IIS site is not contained in the insert, thus it can be cleaved intact from the vector.

TABLE 1

| BstI1 BstXI adapter | |
|---|---|
| CACTGCCTTTCCAGCACA (SEQ IL NO: 16) | Cuts 0 to the left (into the insert) |
| GTGACGGAAAGGTC (SEQ ID NO: 17) | Cuts -2 to left |
| BstDI BstXI adapter | |
| CATTGCCTTTCCAGCACA (SEQ ID NO: 18) | Cuts 0 to left (flush with insert) |
| GTAACGGAAAGGTC (SEQ ID N: 19) | Cuts -2 to left (2 bases into insert) |

Example X

Polymerase Error Rates and the Accuracy of Φ29 Cloning

A problem in estimating the sequence accuracy of DNA cloned by φ29 polymerase rolling circle amplification (RCA) is that there are not good measurements of the overall error rate for the enzyme. The work of Esteban et al. (1993), supra on the fidelity of the enzyme is the most often quoted. However, that paper measures the misinsertion rate for incorrect nucleotides using an exonuclease-deficient mutant. Therefore the proofreading activity of the φ29 polymerase 3' exonuclease is deliberately not included in these measurements. This appears to be ignored in later work (Nelson et al. (2002) *Biotechniques Suppl*, 44-7) that cites Esteban et al. as reporting an error rate of $5\times10^{-6}$. Also, this later work calculates the error rate (ER) as:

$$ER = mf/(bp \times d)$$

where mf is the mutation frequency, bp is the size of the mutational target in base pairs, and d is the number of template doublings. Using this equation the error rate was estimated at $3\times10^{-6}$. But, since the φ29 RCA reaction is not a doubling process, this analysis is inappropriate.

We believe that the true error rate for φ29 polymerase must be $\sim 1\times10^{-6}$ or lower, as it is for other replicative DNA polymerases with proofreading (Esteban (1993), supra; T. A. Kunkel (2004) *J Biol Chem* 279, 16895-8). We have made a number of simplified models of the RCA reaction. For example, consider a four-stage reaction in which 1000 copies are made from the original input molecule. Three consecutive rounds that each gives 100-fold amplification, yielding a total amplification of $10^9$-fold, follow this initial stage. Assuming an error rate of $1\times10^{-6}$ and a 5 kb circular DNA we get:

| Step | Copies | Total bp | New Errors | Propagated Errors | Total Errors | fraction mutant |
|---|---|---|---|---|---|---|
| 0 | 1 | $5 \times 10^3$ | 0 | 0 | 0 | 0% |
| 1 | $10^3$ | $5 \times 10^6$ | 5 | 0 | 5 | 0.5% |
| 2 | $10^5$ | $5 \times 10^8$ | 500 | 500 | 1000 | 1% |//-continued

| Step | Copies | Total bp | New Errors | Propagated Errors | Total Errors | fraction mutant |
|---|---|---|---|---|---|---|
| 3 | $10^7$ | $5 \times 10^{10}$ | $5 \times 10^4$ | $1 \times 10^5$ | $1.5 \times 10^5$ | 1.5% |
| 4 | $10^9$ | $5 \times 10^{12}$ | $5 \times 10^6$ | $1.5 \times 10^7$ | $2 \times 10^7$ | 2% |

By this type of reasoning we predict that the majority of the molecules resulting from $10^9$-fold amplification by the φ29 RCA reaction will be identical to the starting molecule even if the error rate is as high as $10^{-5}$ and the amplification in secondary rounds is as low as 10-fold.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application Ser. No. 60/675,850, filed Apr. 29, 2005, U.S. Provisional Application Ser. No. 60/722,070, filed Sep. 30, 2005, and U.S. Provisional Application Ser. No. 60/725,300, filed Oct. 12, 2005 and in the figures, are hereby incorporated in their entirety by reference.

We claim:

1. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed
with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set; and,
further wherein the random or partially random primers are resistant to exonuclease.

2. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed
with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and,
further wherein at least two nucleotides in each of the primers are linked by a phosphorothioate linkage.

3. A method for amplifying a DNA template, comprising contacting a DNA with a strand-displacing, processive DNA polymerase and a set of random or partially random primers, under conditions that are effective for promoting DNA strand displacement, at an isothermal temperature, wherein the amplification is performed
with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and, further wherein the DNA template is a single copy.

4. The method of claim 1, wherein the amplification is performed in a volume of 3 µl or less.

5. The method of claim 1, wherein the amplification is performed in a volume of 0.6 µl or less.

6. The method of claim 1, wherein the amplification is performed in a single reaction, and the DNA template is amplified by a factor of at least, or about $10^9$.

7. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed
with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and,
wherein the ratio of polymerase to template is about $1.5 \times 10^{11}:1$ or less; and,
further wherein the DNA template is amplified by multiple displacement amplification (MDA).

8. A method for amplifying a DNA template, comprising contacting a DNA with a strand-displacing, processive DNA polymerase and a set of random or partially random primers, under conditions that are effective for promoting DNA strand displacement at an isothermal temperature,
wherein the amplification is performed
a) with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and,
further wherein the DNA template is a single-stranded circle, and the amplification is by rolling circle amplification (RCA).

9. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed
with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and,
further wherein the DNA polymerase is a φ29-type polymerase or φ29 polymerase.

10. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed
a) with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and,
further wherein the method is performed in an automated nanomolar system.

11. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed
a) with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set, and
b) in a volume of 5 µl or less, wherein the random or partially random primers are resistant to exonuclease.

12. A method for amplifying a DNA template, comprising contacting a DNA with a strand-displacing, processive DNA polymerase and a set of random or partially random primers, under conditions that are effective for promoting DNA strand displacement, at an isothermal temperature,
wherein the amplification is performed with a primer set in which the primers cannot base pair their 3' nucleotides with other copies of the primers, wherein if the 3' terminal nucleotide of the primer set is A, the nucleotide T is not present at any position in the primer set; if the 3' terminal nucleotide of the primer set is T, the nucleotide A is not present at any position in the primer set; if the 3' terminal nucleotide of the primer set is C, the nucleotide G is not present at any position in the primer set; and if the 3' terminal nucleotide of the primer set is G, the nucleotide C is not present at any position in the primer set.

13. The method of claim 12, further wherein the random or partially random primers are resistant to exonuclease.

14. The method of claim 12, further wherein at least two nucleotides in each of the primers are linked by a phosphorothioate linkage.

15. The method of claim 12, further wherein the DNA template is a single copy.

16. The method of claim 11, further wherein the amplification is performed in a single reaction, and the DNA template is amplified by a factor of at least, or about $10^9$.

17. The method of claim 11, further wherein the DNA template is amplified by multiple displacement amplification (MDA).

18. The method of claim 11, further wherein the DNA template is a single-stranded circle, and the amplification is by rolling circle amplification (RCA).

19. The method of claim 11, further wherein the DNA polymerase is a φ29-type polymerase or φ29 polymerase.

20. The method of claim 11, further wherein the method is performed in an automated nanomolar system.

21. The method of claim 12, further wherein the amplification is performed in a single reaction, and the DNA template is amplified by a factor of at least, or about $10^9$.

22. The method of claim 12, further wherein the DNA template is amplified by multiple displacement amplification (MDA).

23. The method of claim 12, further wherein the DNA template is a single-stranded circle, and the amplification is by rolling circle amplification (RCA).

24. The method of claim 12, further wherein the DNA polymerase is a φ29-type polymerase or φ29 polymerase.

25. The method of claim 12, further wherein the method is performed in an automated nanomolar system.

* * * * *